(12) United States Patent
Vratsanos et al.

(10) Patent No.: US 7,528,111 B2
(45) Date of Patent: May 5, 2009

(54) METHOD OF VACCINATING SUBJECTS RECEIVING IMMUNE MODULATING THERAPY

(75) Inventors: George Vratsanos, Yardley, PA (US); Francisco Leon, Bethesda, MD (US); Lee K. Tay, Princeton Junction, NJ (US); Kenneth M. Bahrt, Edison, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/800,860

(22) Filed: May 8, 2007

(65) Prior Publication Data

US 2008/0019999 A1    Jan. 24, 2008

Related U.S. Application Data

(60) Provisional application No. 60/799,981, filed on May 12, 2006, provisional application No. 60/848,078, filed on Sep. 28, 2006.

(51) Int. Cl.
*A61K 38/16* (2006.01)
*C07K 14/435* (2006.01)
*C07K 14/705* (2006.01)

(52) U.S. Cl. ............... 514/12; 424/134.1; 530/350; 530/387.3

(58) Field of Classification Search ............... None
See application file for complete search history.

(56) References Cited

U.S. PATENT DOCUMENTS

| | | | |
|---|---|---|---|
| 5,434,131 | A | 7/1995 | Linsley et al. |
| 5,773,253 | A | 6/1998 | Linsley et al. |
| 5,844,095 | A | 12/1998 | Linsley et al. |
| 5,851,795 | A | 12/1998 | Linsley et al. |
| 6,090,914 | A | 7/2000 | Linsley et al. |
| 7,094,874 | B2 | 8/2006 | Peach et al. |
| 2002/0182211 | A1 | 12/2002 | Peach et al. |
| 2003/0083246 | A1 | 5/2003 | Cohen et al. |
| 2004/0022787 | A1 | 2/2004 | Cohen et al. |
| 2007/0009511 | A1 | 1/2007 | Hagerty et al. |

FOREIGN PATENT DOCUMENTS

WO    WO2002/02638    1/2002

OTHER PUBLICATIONS

Ruderman et al., Arthtritis Res. Ther., 2005, 7(Suppl.2): S21-S25.*
LInsley, P. et al., "Human B7-1 (CD80) and B7-2 (CD86) Bind with Similar Avidities but Distinct Kinetics to CD28 and CTLA-4 Receptors", Immunity, vol. 1, pp. 793-801 (1994).
Manghi. M. et al., "Development of an ELISA for measuring the activity of tetanus toxoid in vaccines and comparison with the toxin neutralization test in mice", J. of Immunological Methods, vol. 168, pp. 17-24 (1994).
Oaks, M. et al., "A Native Soluble Form of CTLA-4", Cellular Immunology, vol. 201, pp. 144-153 (2000).
Peach, R. et al., "Complementarity Determining Region 1 (CDR1)- and CDR3-analogous Regions in CTLA-4 and CD28 Determine the Binding to B7-1", J. Exp. Med., vol. 180, pp. 2049-2058 (1994).
Wernette, C. et al., "Enzyme-Linked Immunosorbent Assay for Quantitation of Human Antibodies to Pneumococcal Polysaccharides", Clinical and Diagnostic Laboratory Immunology, vol. 10(4), pp. 514-519 (2003).
Corbo, M. et al., "A single dose of abatacept does not prevent the development of a positive immune response to tetanus and pneumococcal vaccines", Ann Rheum Dis. vol. 65(Suppl-II) p. 184, (2006).
Elkayam, O. et al., "The Effect of Tumor Necrosis Factor Blockade on the Response to Pneumococcal Vaccination in Patients with Rheumatoid Arthritis and Ankylosing Spondylitis", Semin Arthritis Rheum, vol. 33, pp. 283-288 (2004).
Glück, T., "Vaccinate your immunocompromised patients!", Rheumatology, vol. 45, pp. 9-10 (2006).
McIntyre, J.A., et al., "Belatacept-Treatment of transplant rejection", Drugs of the Future, vol. 30(9), pp. 873-876 (2005).
Tay, L. et al., "Vaccination response to tetanus toxoid and 23-valent pneumococcal vaccines following administration of a single dose of abatacept: a randomized, open-label, parallel group study in healthy subjects", Arthritis Research & Therapy, vol. 9(2), p. R38, (2007).
Vital, E. et al., "Abatacept", Drugs of Today, vol. 42(2), pp. 87-93 (2006).
Zimmermann, C. et al., "Antiviral Immune Responses in CTLA4 Transgenic Mice", Journal of Virology, vol. 71(3), pp. 1802-1807 (1997).

* cited by examiner

*Primary Examiner*—Ilia Ouspenski
(74) *Attorney, Agent, or Firm*—Nickki L. Parlet

(57) ABSTRACT

The present invention relates to methods of vaccinating subjects receiving immune modulating therapy, such as soluble CTLA4 molecules, for treatment of immune system diseases mediated by T-cell interactions with B7-positive cells including, but not limited to, autoimmune diseases, immunoproliferative diseases, and immune disorders associated with graft transplantation.

12 Claims, 8 Drawing Sheets

Study design

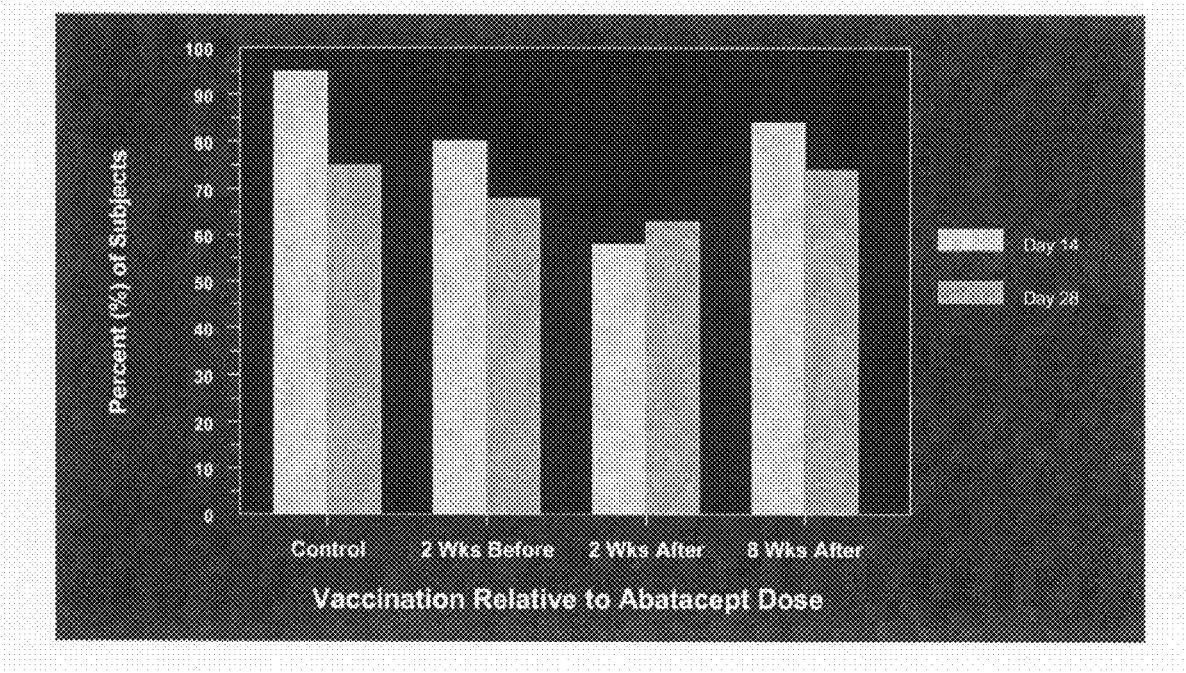

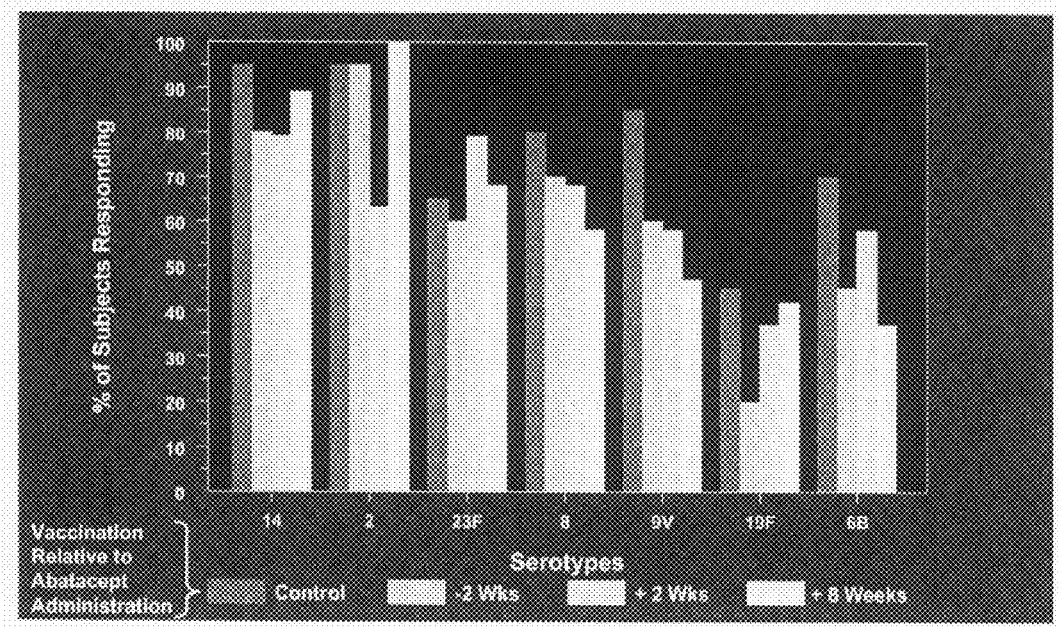

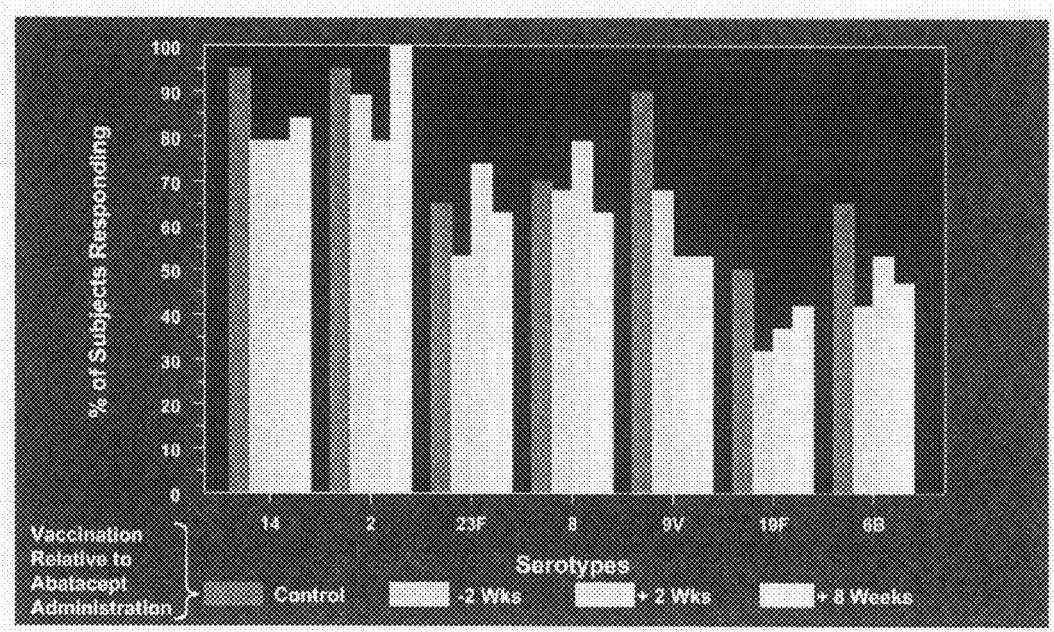

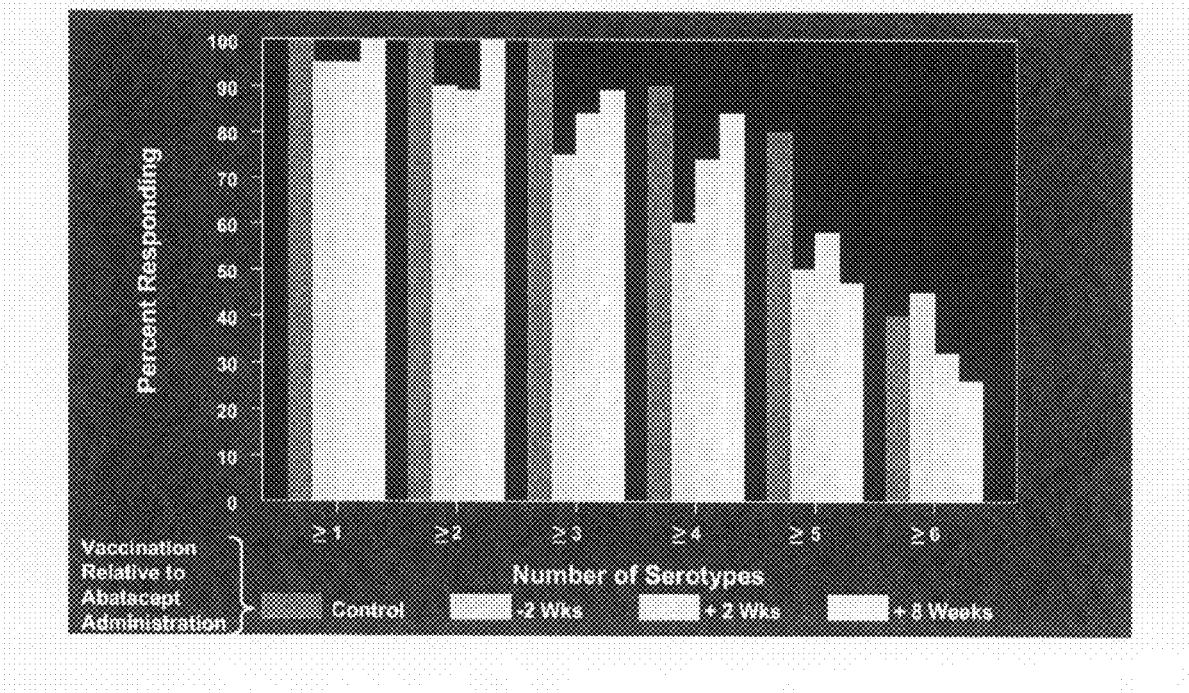

FIG. 6

| | |
|---|---|
| ATGGGTGTACTGCTCACACAGAGGACGCTGCTCAGTCTGGTCCTTGCACTCCTGTTTCCA | -19 |
| M~~G~~V~~L~~L~~T~~Q~~R~~T~~L~~L~~S~~L~~V~~L~~A~~L~~L~~F~~P~~ | -7 |
| AGCATGGCGAGCATGGCAATGCACGTGGCCCAGCCTGCTGTGGTACTGGCCAGCAGCCGA | +42 |
| S~~M~~A~~S~~M~~A~~M~~H~~V~~A~~Q~~P~~A~~V~~V~~L~~A~~S~~S~~R~~ | +14 |
|             +1 | |
| GGCATCGCTAGCTTTGTGTGTGAGTATGCATCTCCAGGCAAAGCCACTGAGGTCCGGGTG | +102 |
| G~~I~~A~~S~~F~~V~~C~~E~~Y~~A~~S~~P~~G~~K~~A~~T~~E~~V~~R~~V~~ | +34 |
| ACAGTGCTTCGGCAGGCTGACAGCCAGGTGACTGAAGTCTGTGCGGCAACCTACATGATG | +162 |
| T~~V~~L~~R~~Q~~A~~D~~S~~Q~~V~~T~~E~~V~~C~~A~~A~~T~~Y~~M~~M~~ | +54 |
| GGGAATGAGTTGACCTTCCTAGATGATTCCATCTGCACGGGCACCTCCAGTGGAAATCAA | +222 |
| G~~N~~E~~L~~T~~F~~L~~D~~D~~S~~I~~C~~T~~G~~T~~S~~S~~G~~N~~Q~~ | +74 |
| GTGAACCTCACTATCCAAGGACTGAGGGCCATGGACACGGGACTCTACATCTGCAAGGTG | +282 |
| V~~N~~L~~T~~I~~Q~~G~~L~~R~~A~~M~~D~~T~~G~~L~~Y~~I~~C~~K~~V~~ | +94 |
| GAGCTCATGTACCCACCGCCATACTACCTGGGCATAGGCAACGGAACCCAGATTTATGTA | +342 |
| E~~L~~M~~Y~~P~~P~~P~~Y~~Y~~L~~G~~I~~G~~N~~G~~T~~Q~~I~~Y~~V~~ | +114 |
| ATTGATCCAGAACCGTGCCCAGATTCTGATCAGGAGCCCAAATCTTCTGACAAAACTCAC | +402 |
| I~~D~~P~~E~~P~~C~~P~~D~~S~~D~~Q~~E~~P~~K~~S~~S~~D~~K~~T~~H~~ | +134 |
| ACATCCCCACCGTCCCCAGCACCTGAACTCCTGGGTGGATCGTCAGTCTTCCTCTTCCCU | +462 |
| T~~S~~P~~P~~S~~P~~A~~P~~E~~L~~L~~G~~G~~S~~S~~V~~F~~L~~F~~P~~ | +154 |
| CCAAAACCCAAGGACACCCTCATGATCTCCCGGACCCCTGAGGTCACATGCGTGGTGGTG | +522 |
| P~~K~~P~~K~~D~~T~~L~~M~~I~~S~~R~~T~~P~~E~~V~~T~~C~~V~~V~~V~~ | +174 |
| GACGTGAGCCACGAAGACCCTGAGGTCAAGTTCAACTGGTACGTGGACGGCGTGGAGGTG | +582 |
| D~~V~~S~~H~~E~~D~~P~~E~~V~~K~~F~~N~~W~~Y~~V~~D~~G~~V~~E~~V~~ | +194 |
| CATAATGCCAAGACAAAGCCGCGGGAGGAGCAGTACAACAGCACGTACCGGGTGGTCAGC | +642 |
| H~~N~~A~~K~~T~~K~~P~~R~~E~~E~~Q~~Y~~N~~S~~T~~Y~~R~~V~~V~~S~~ | +214 |
| GTCCTCACCGTCCTGCACCAGGACTGGCTGAATGGCAAGGAGTACAAGTGCAAGGTCTCC | +702 |
| V~~L~~T~~V~~L~~H~~Q~~D~~W~~L~~N~~G~~K~~E~~Y~~K~~C~~K~~V~~S~~ | +234 |
| AACAAAGCCCTCCCAGCCCCCATCGAGAAAACCATCTCCAAAGCCAAAGGGCAGCCCCGA | +762 |
| N~~K~~A~~L~~P~~A~~P~~I~~E~~K~~T~~I~~S~~K~~A~~K~~G~~Q~~P~~R~~ | +254 |
| GAACCACAGGTGTACACCCTGCCCCCATCCCGGGATGAGCTGACCAAGAACCAGGTCAGC | +822 |
| E~~P~~Q~~V~~Y~~T~~L~~P~~P~~S~~R~~D~~E~~L~~T~~K~~N~~Q~~V~~S~~ | +274 |
| CTGACCTGCCTGGTCAAAGGCTTCTATCCCAGCGACATCGCCGTGGAGTGGGAGAGCAAT | +882 |
| L~~T~~C~~L~~V~~K~~G~~F~~Y~~P~~S~~D~~I~~A~~V~~E~~W~~E~~S~~N~~ | +294 |
| GGGCAGCCGGAGAACAACTACAAGACCACGCCTCCCGTGCTGGACTCCGACGGCTCCTTC | +942 |
| G~~Q~~P~~E~~N~~N~~Y~~K~~T~~T~~P~~P~~V~~L~~D~~S~~D~~G~~S~~F~~ | +314 |
| TTCCTCTACAGCAAGCTCACCGTGGACAAGAGCAGGTGGCAGCAGGGGAACGTCTTCTCA | +1002 |
| F~~L~~Y~~S~~K~~L~~T~~V~~D~~K~~S~~R~~W~~Q~~Q~~G~~N~~V~~F~~S~~ | +334 |
| TGCTCCGTGATGCATGAGGCTCTGCACAACCACTACACGCAGAAGAGCCTCTCCCTGTCT | +1062 |
| C~~S~~V~~M~~H~~E~~A~~L~~H~~N~~H~~Y~~T~~Q~~K~~S~~L~~S~~L~~S~~ | +354 |
| CCGGGTAAATGA | |
| P~~G~~K~~* | |

FIG. 7

```
ONCOSTATIN M SIGNAL PEPTIDE
 M   G   V   L   L   T   Q   R   T   L   L   S   L   V   L
ATG GGT GTA CTG CTC ACA CAG AGG ACG CTG CTC AGT CTG GTC CTT    45
                                  ← -1 ⏋ +1

A   L   L   F   P   S   M   A   S   M   A   M   H   V   A
GCA CTC CTG TTT CCA AGC ATG GCG AGC ATG GCA ATG CAC GTG GCC    90

Q   P   A   V   V   L   A   S   S   R   G   I   A   S   F
CAG CCT GCT GTG GTA CTG GCC AGC AGC CGA GGC ATC GCC AGC TTT   135

V   C   E   Y   A   S   P   G   K   A   T   E   V   R   V
GTG TGT GAG TAT GCA TCT CCA GGC AAA GCC ACT GAG GTC CGG GTG   180

T   V   L   R   Q   A   D   S   Q   V   T   E   V   C   A
ACA GTG CTT CGG CAG GCT GAC AGC CAG GTG ACT GAA GTC TGT GCG   225

A   T   Y   M   M   G   N   E   L   T   F   L   D   D   S
GCA ACC TAC ATG ATG GGG AAT GAG TTG ACC TTC CTA GAT GAT TCC   270

I   C   T   G   T   S   S   G   N   Q   V   N   L   T   I
ATC TGC ACG GGC ACC TCC AGT GGA AAT CAA GTG AAC CTC ACT ATC   315

Q   G   L   R   A   M   D   T   G   L   Y   I   C   K   V
CAA GCA CTG AGG GCC ATG GAC ACG GGA CTC TAC ATC TGC AAG GTG   360
                                           GLYCOSYLATION SITE
                                                   ⎡
 E   L   M   Y   P   P   P   Y   Y   L   G   I   G   N   G
GAG CTC ATG TAC CCA CCG CCA TAC TAC CTG GGC ATA GGC AAC GGA   405
←⏋
 T   Q   I   Y   V   I   D   P   E   P   C   P   D   S   D
ACC CAG ATT TAT GTA ATT GAT CCA GAA CCG TGC CCA GAT TCT GAC   450

F   L   L   W   I   L   A   A   V   S   S   G   L   F   F
TTC CTC CTC TGG ATC CTT GCA GCA GTT AGT TCG GGG TTG TTT TTT   495

Y   S   F   L   L   T   A   V   S   L   S   K   M   L   K
TAT AGC TTT CTC CTC ACA GCT GTT TCT TTG AGC AAA ATG CTA AAG   540

K   R   S   P   L   T   T   G   V   Y   V   K   M   P   P
AAA AGA AGC CCT CTT ACA ACA GGG GTC TAT GTG AAA ATG CCC CCA   585

T   E   P   E   C   E   K   Q   F   Q   P   Y   F   I   P
ACA GAG CCA GAA TGT GAA AAG CAA TTT CAG CCT TAT TTT ATT CCC   630

I   N
ATC AAT                                                       636
```

FIG. 8

```
ATGGGTGTACTGCTCACACAGAGGACGCTGCTCAGTCTGGTCCTTGCACTCCTGTTTCCA      -19
M~~G~~V~~L~~L~~T~~Q~~R~~T~~L~~L~~S~~L~~V~~L~~A~~L~~L~~F~~P~~      -7

AGCATGGCGAGCATGGCAATGCACGTGGCCCAGCCTGCTGTGGTACTGGCCAGCAGCCGA      +42
S~~M~~A~~S~~M~~A~~M~~H~~V~~A~~Q~~P~~A~~V~~V~~L~~A~~S~~S~~R~~      +14
                 +1

GGCATCGCTAGCTTTGTGTGTGAGTATGCATCTCCAGGCAAATATACTGAGGTCCGGGTG     +102
G~~I~~A~~S~~F~~V~~C~~E~~Y~~A~~S~~P~~G~~K~~Y~~T~~E~~V~~R~~V~~      +34

ACAGTGCTTCGGCAGGCTGACAGCCAGGTGACTGAAGTCTGTGCGGCAACCTACATGATG     +162
T~~V~~L~~R~~Q~~A~~D~~S~~Q~~V~~T~~E~~V~~C~~A~~A~~T~~Y~~M~~M~~      +54

GGGAATGAGTTGACCTTCCTAGATGATTCCATCTGCACGGGCACCTCCAGTGGAAATCAA     +222
G~~N~~E~~L~~T~~F~~L~~D~~D~~S~~I~~C~~T~~G~~T~~S~~S~~G~~N~~Q~~      +74

GTGAACCTCACTATCCAAGGACTGAGGGCCATGGACACGGGACTCTACATCTGCAAGGTG     +282
V~~N~~L~~T~~I~~Q~~G~~L~~R~~A~~M~~D~~T~~G~~L~~Y~~I~~C~~K~~V~~      +94

GAGCTCATGTACCCACCGCCATACTACGAGGGCATAGGCAACGGAACCCAGATTTATGTA     +342
E~~L~~M~~Y~~P~~P~~P~~Y~~Y~~E~~G~~I~~G~~N~~G~~T~~Q~~I~~Y~~V~~     +114

ATTGATCCAGAACCGTGCCCAGATTCTGATCAGGAGCCCAAATCTTCTGACAAAACTCAC     +402
I~~D~~P~~E~~P~~C~~P~~D~~S~~D~~Q~~E~~P~~K~~S~~S~~D~~K~~T~~H~~     +134

ACATCCCCACCGTCCCCAGCACCTGAACTCCTGGGGGGATCGTCAGTCTTCCTCTTCCCC     +462
T~~S~~P~~P~~S~~P~~A~~P~~E~~L~~L~~G~~G~~S~~S~~V~~F~~L~~F~~P~~     +154

CCAAAACCCAAGGACACCCTCATGATCTCCCGGACCCCTGAGGTCACATGCGTGGTGGTG     +522
P~~K~~P~~K~~D~~T~~L~~M~~I~~S~~R~~T~~P~~E~~V~~T~~C~~V~~V~~V~~     +174

GACGTGAGCCACGAAGACCCTGAGGTCAAGTTCAACTGGTACGTGGACGGCGTGGAGGTG     +582
D~~V~~S~~H~~E~~D~~P~~E~~V~~K~~F~~N~~W~~Y~~V~~D~~G~~V~~E~~V~~     +194

CATAATGCCAAGACAAAGCCGCGGGAGGAGCAGTACAACAGCACGTACCGTGTGGTCAGC     +642
H~~N~~A~~K~~T~~K~~P~~R~~E~~E~~Q~~Y~~N~~S~~T~~Y~~R~~V~~V~~S~~     +214

GTCCTCACCGTCCTGCACCAGGACTGGCTGAATGGCAAGGAGTACAAGTGCAAGGTCTCC     +702
V~~L~~T~~V~~L~~H~~Q~~D~~W~~L~~N~~G~~K~~E~~Y~~K~~C~~K~~V~~S~~     +234

AACAAAGCCCTCCCAGCCCCCATCGAGAAAACCATCTCCAAAGCCAAAGGGCAGCCCCGA     +762
N~~K~~A~~L~~P~~A~~P~~I~~E~~K~~T~~I~~S~~K~~A~~K~~G~~Q~~P~~R~~     +254

GAACCACAGGTGTACACCCTGCCCCCATCCCGGGATGAGCTGACCAAGAACCAGGTCAGC     +822
E~~P~~Q~~V~~Y~~T~~L~~P~~P~~S~~R~~D~~E~~L~~T~~K~~N~~Q~~V~~S~~     +274

CTGACCTGCCTGGTCAAAGGCTTCTATCCCAGCGACATCGCCGTGGAGTGGGAGAGCAAT     +882
L~~T~~C~~L~~V~~K~~G~~F~~Y~~P~~S~~D~~I~~A~~V~~E~~W~~E~~S~~N~~     +294

GGGCAGCCGGAGAACAACTACAAGACCACGCCTCCCGTGCTGGACTCCGACGGCTCCTTC     +942
G~~Q~~P~~E~~N~~N~~Y~~K~~T~~T~~P~~P~~V~~L~~D~~S~~D~~G~~S~~F~~     +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~     +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~     +354

CCGGGTAAATGA
P~~G~~K~~*
```

US 7,528,111 B2

METHOD OF VACCINATING SUBJECTS RECEIVING IMMUNE MODULATING THERAPY

The present patent application claims the priority of U.S. Ser. No. 60/799,981, filed on May 12, 2006 and U.S. Ser. No. 60/848,078, filed on Sep. 28, 2006, which is hereby incorporated by reference in its entirety.

Throughout this application various publications are referenced. The disclosures of these publications in their entireties are hereby incorporated by reference into this application in order to more fully describe the state of the art to which this invention pertains.

FIELD OF THE INVENTION

The present invention relates to methods of vaccinating subjects receiving immune modulating therapy, such as soluble CTLA4 molecules, for treatment of immune system diseases mediated by T-cell interactions with B7-positive cells including, but not limited to, autoimmune diseases, immunoproliferative diseases, and immune disorders associated with graft transplantation.

BACKGROUND OF THE INVENTION

Vaccine-induced immunity requires an intact immune system for optimal response and development of protective immunity. Since there is now almost universal vaccination from infancy for prevention of tetanus and infections of pneumococcal origin, it follows that new immune system regulating therapies should be studied for their effect on the ability to mount a productive antibody response to these vaccines. Depending on the type of vaccines administered, the antibody response generated is considered to be either relatively T-cell dependent or T-cell independent. Vaccines, such as tetanus toxoid, elicit a humoral response that is influenced by T cells and is considered T-cell dependent. Other vaccines, like pneumococcal vaccines, do not require T cells to induce an antibody response and are considered T-cell independent. However, T cells do contribute to the intensity of the antibody response and thus this response cannot be considered completely T-cell independent.

T-cell independent antigens (e.g. 23-valent pneumococcal vaccine) are typically polysaccharide in origin and can bind directly to receptors on the surface of B cells, thereby eliciting B cell differentiation and proliferation without an absolute requirement for T cell help. This applies to both primary and secondary responses to polysaccharide antigens. The 23-valent pneumococcal vaccine is recommended for patients at risk for developing pneumococcal infections (such as patients with sickle cell anemia, diabetes mellitus, chronic cardiovascular or pulmonary disorders, immunocompromised patients, and all adults over the age of 65 years).

Measurement of specific antibody production in response to a vaccine is a means of evaluating B cell function and helper T cell function. The antibody response to an antigen involves the presentation of the antigen via an antigen-presenting cell (APC) to helper T cells. These T cells then interact with B cells via the B cell receptor (cell surface IgM/IgG specific for the antigen) and "second signal" receptor ligand pairs to induce B cell activation and proliferation resulting in specific antibody production. Specific antibody production following vaccinations is measured at the pre-vaccine and post-vaccine serum antibody levels. The post-vaccine antibody levels are typically obtained 2-4 weeks after vaccination.

Treatment with CTLA4Ig has been shown to improve the signs and symptoms of rheumatoid arthritis (RA). This has been shown in patients with active RA who have had an inadequate responses to methotrexate and also in patients with inadequate responses to anti-tumor necrosis factor therapy. CTLA4Ig treats RA by selectively modulating the CD80/CD86: CD28 costimulatory signal required for T-cell (T-lymphocyte) activation. This selective co-stimulation modulator inhibits T-cell activation by binding to CD80 and CD86, thereby blocking a costimulatory signal necessary for full activation of T cells, implicated in the pathogenesis of RA.

Timing of vaccine administration in relation to illnesses, other vaccines, and certain medications is recognized as important to the appropriate use of vaccines. With agents such as soluble CTLA4 molecules that affect T-cell activation, the timing of vaccine administration (pre-/post-CTLA4 dose) may affect the magnitude of the immune response. The effect of soluble CTLA4 molecules on response to therapeutic vaccines has not been previously evaluated.

SUMMARY OF INVENTION

The present invention relates to methods of vaccinating subjects receiving immune modulating therapy, such as soluble CTLA4 molecules, for treatment of immune system diseases mediated by T-cell interactions with B7-positive cells including, but not limited to, autoimmune diseases, immunoproliferative diseases, and immune disorders associated with graft transplantation.

One embodiment of the invention is a method of vaccinating a subject being treated with soluble CTLA4 molecule comprising administering a vaccine 14±3 days prior to the administration of the soluble CTLA4 molecule dose, or 14±3 days after the administration of the soluble CTLA4 molecule dose, or 7±3 days prior to the administration of the soluble CTLA4 molecule dose, or at least 4 days prior to the administration of the soluble CTLA4 molecule dose, or at a low point of the effective serum trough concentration of the soluble CTLA4 molecule.

One embodiment of the invention is a method of vaccinating a subject being treated with soluble CTLA4 molecule wherein the soluble CTLA4 molecule is CTLA4Ig as shown in FIG. 6 beginning with methionine at position +1 or with alanine at position −1 and ending with lysine at position +357 or glycine at position +356.

One embodiment of the invention is a method of vaccinating a subject being treated with soluble CTLA4 molecule wherein the soluble CTLA4 molecule is L104EA29YIg as shown in FIG. 8 beginning with methionine at position +1 or with alanine at position −1 and ending with lysine at position +357 or glycine at position +356.

One embodiment of the invention is a method of vaccinating a subject being treated with soluble CTLA4 molecule comprising administering a vaccine 7±3 days prior to the administration of the soluble CTLA4 molecule dose, wherein the soluble CTLA4 molecule is CTLA4Ig as shown in FIG. 6 beginning with methionine at position +1 or with alanine at position −1 and ending with lysine at position +357 or glycine at position +356, and wherein the CTLA4Ig dose is 500 mg for a subject weighing less than 60 kg, 750 mg for a subject weighting between 60-100 kg and 1000 mg for a subject weighing more than 100 kg.

One embodiment of the invention is a method of vaccinating a subject being treated with soluble CTLA4 molecule comprising administering a vaccine 7±3 days prior to the administration of the soluble CTLA4 molecule dose, wherein the soluble CTLA4 molecule is L104EA29YIg as shown in FIG. 8 beginning with methionine at position +1 or with alanine at position −1 and ending with lysine at position +357 or glycine at position +356, and wherein the L104EA29YIg dose is 5 mg/kg weight of the subject.

One embodiment of the invention is a method for treating a subject comprising administering an effective dose of soluble CTLA4 molecule, which comprises an extracellular domain of a CTLA4 molecule, wherein the extracellular domain of the CTLA4 moleucle comprises the amino acids shown in FIG. 7 beginning with methionine at position +1 or with alanine at position −1 and ending with aspartic acid at position +124; and administering a vaccine.

Another embodiment of the invention is a method for treating a subject by administering a vaccine 7±3 days prior to the administration of the soluble CTLA4 molecule dose.

Another embodiment of the invention is a method for treating subjects having an immune system disease comprising administering an effective dose of soluble CTLA4 molecule comprising an extracellular domain of a CTLA4 molecule, wherein the extracellular domain of the CTLA4 moleucle comprises the amino acids shown in FIG. 7 beginning with methionine at position +1 or with alanine at position −1 and ending with aspartic acid at position +124 and administering a vaccine 7±3 days prior to the administration of the soluble CTLA4 molecule dose.

Another embodiment of the invention is a method for treating subjects having rheumatic disease comprising administering an effective dose of CTLA4Ig as shown in FIG. 6 beginning with methionine at position +1 or with alanine at position −1 and ending with lysine at position +357 or glycine at position +356, and administering a vaccine 7±3 days prior to the administration of the CTLA4Ig dose.

Another embodiment of the invention is a method for treating immune disorders associated with graft transplantation rejection comprising administering to a subject an effective dose of L104EA29YIg as shown in FIG. 8 beginning with methionine at position +1 or with alanine at position −1 and ending with lysine at position +357 or glycine at position +356, and administering a vaccine 7±3 days prior to the administration of the L104EA29YIg dose.

In another embodiment, the vaccine is selected from the group consisting of influenza vaccine, pneumococcal vaccine and tetanus toxoid vaccine.

In another embodiment, the soluble CTLA4 molecule is administered in an amount between about 0.1 and about 20.0 mg/kg weight of the subject.

In another embodiment, the effective trough serum concentration of the soluble CTLA4 molecules is between about 0.2 µg/mL and about 70 µg/mL.

BRIEF DESCRIPTION OF THE FIGURES

FIG. 2 shows the percent of subjects on Day 28 achieving a ≧2-fold increase in tetanus toxoid antibody from baseline as described in Example 1.

FIG. 3 shows the percentage of subjects with ≧2-fold increase to individual serotypes on Day 14 after vaccination as described in Example 1.

FIG. 4 shows the percentage of subjects with ≧2-fold increase to individual serotypes on Day 28 after vaccination as described in Example 1.

FIG. 5 shows the number of serotypes to which subjects responded on Day 14 after vaccination as described in Example 1.

FIG. 6 shows the nucleotide and amino acid sequence of CTLA4Ig (SEQ ID NO: 1 and SEQ ID NO: 2, respectively).

FIG. 7 shows the nucleotide and amino acid sequence of CTLA4 receptor (SEQ ID NO: 3 and SEQ ID NO: 4, respectively).

FIG. 8 shows the nucleotide and amino acid sequence of L104EA29YIg (SEQ ID NO: 5 and SEQ ID NO: 6, respectively).

DETAILED DESCRIPTION OF THE INVENTION

Definitions

Figure 1:
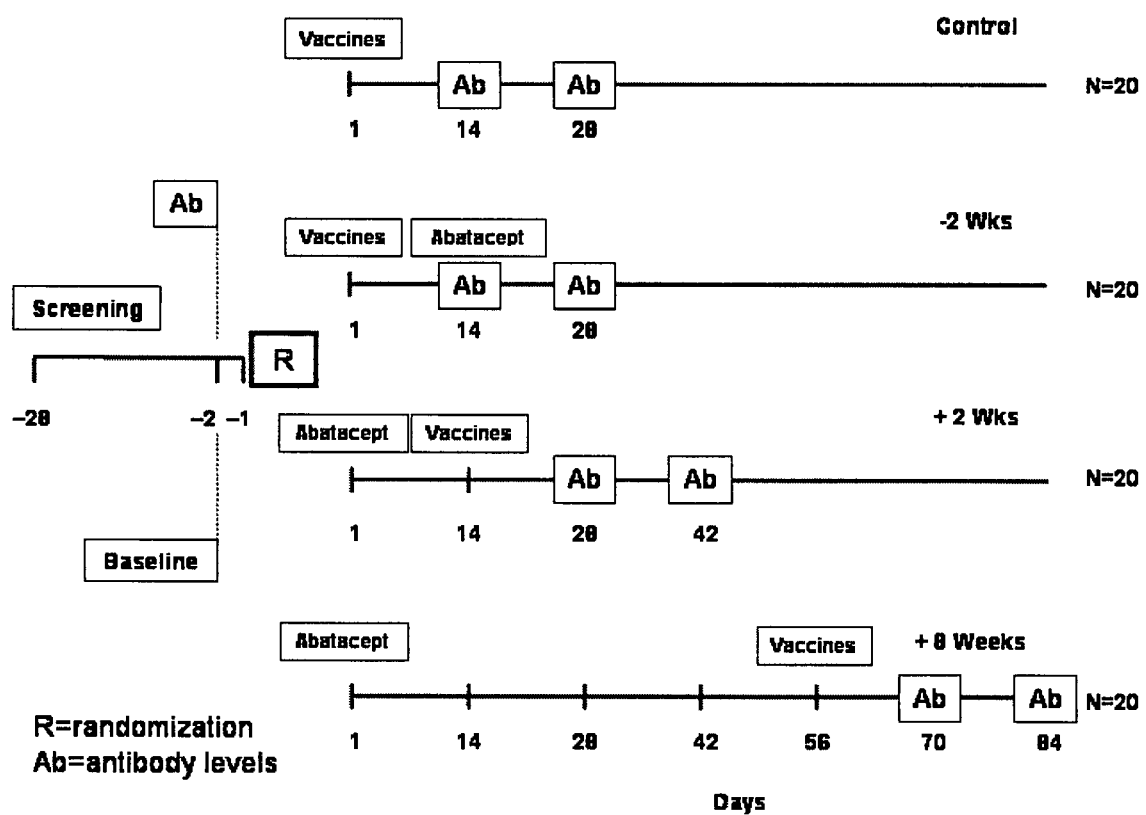
FIG. 1 shows the study design for the experiment described in Example 1.

All scientific and technical terms used in this application have meanings commonly used in the art unless otherwise specified. As used in this application, the following words or phrases have the meanings specified.

As used herein "wild type CTLA4" or "non-mutated CTLA4" has the amino acid sequence of naturally occurring, full length CTLA4 as shown in FIG. 7 (also as described in U.S. Pat. Nos. 5,434,131, 5,844,095, and 5,851,795 herein incorporated by reference in their entirety), or any portion or derivative thereof, that recognizes and binds a B7 or interferes with a B7 so that it blocks binding to CD28 and/or CTLA4 (e.g., endogenous CD28 and/or CTLA4). In particular embodiments, the extracellular domain of wild type CTLA4 begins with methionine at position +1 and ends at aspartic acid at position +124, or the extracellular domain of wild type CTLA4 begins with alanine at position −1 and ends at aspartic acid at position +124 as shown in FIG. 23. Wild type CTLA4 is a cell surface protein, having an N-terminal extracellular domain, a transmembrane domain, and a C-terminal cytoplasmic domain. The extracellular domain binds to target molecules, such as a B7 molecule. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. Alternatively, the signal peptide may not be removed completely, generating molecules that begin before the common starting amino acid methionine. Thus, the mature CTLA4 protein may start at methionine at position +1 or alanine at position −1. The mature form of the CTLA4 molecule includes the extracellular domain or any portion thereof, which binds to B7.

As used herein "CTLA4Ig" is a soluble fusion protein comprising an extracellular domain of wildtype CTLA4 joined to an Ig tail, or a portion thereof that binds a B7. A particular embodiment comprises the extracellular domain of wild type CTLA4 (as shown in FIG. 6) starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 or glycine at position +356 (DNA encoding CTLA4Ig was deposited on May 31, 1991 with the American Type Culture Collection (ATCC), 10801 University Blvd., Manassas, Va. 20110-2209 under the provisions of the Budapest Treaty, and has been accorded ATCC accession number ATCC 68629; Linsley, P., et al., *Immunity*, 1:793-80 (1994). CTLA4Ig-24, a Chinese Hamster Ovary (CHO) cell line expressing CTLA4Ig was deposited on May 31, 1991 with ATCC identification number CRL-10762). The soluble CTLA4Ig molecules may or may not include a signal (leader) peptide sequence.

As used herein, "soluble" refers to any molecule, or fragments and derivatives thereof, not bound or attached to a cell, i.e., circulating. For example, CTLA4, B7 or CD28 can be made soluble by attaching an immunoglobulin (Ig) moiety to the extracellular domain of CTLA4, B7 or CD28, respectively. Alternatively, a molecule such as CTLA4 can be rendered soluble by removing its transmembrane domain. Typically, the soluble molecules used in the methods, compositions and/or kits of the invention do not include a signal (or leader) sequence.

As used herein, "soluble CTLA4 molecules" means non-cell-surface-bound (i.e. circulating) CTLA4 molecules or any functional portion of a CTLA4 molecule that binds B7 including, but not limited to: CTLA4Ig fusion proteins (e.g. encoded by DNA deposited with ATCC accession number 68629), wherein the extracellular domain of CTLA4 is fused to an immunoglobulin (Ig) moiety such as IgCγ1 (IgC-gamma1), IgCγ2 (IgCgamma2), IgCγ3 (IgCgamma3), IgCγ4 (IgCgamma4), IgCµ(IgCmu), IgCα1 (IgCalpa1), IgCα2 (Ig-Calpha2), IgCδ(IgCdelta) or IgCε(IgCepsilon), rendering the fusion molecule soluble, or fragments and derivatives thereof; proteins with the extracellular domain of CTLA4 fused or joined with a portion of a biologically active or chemically active protein such as the papillomavirus E7 gene product (CTLA4-E7), melanoma-associated antigen p97 (CTLA4-p97) or HIV env protein (CTLA4-env gp120) (as described in U.S. Pat. No. 5,844,095, herein incorporated by reference in its entirety), or fragments and derivatives thereof; hybrid (chimeric) fusion proteins such as CD28/CTLA4Ig (as described in U.S. Pat. No. 5,434,131, herein incorporated by reference in its entirety), or fragments and derivatives thereof; CTLA4 molecules with the transmembrane domain removed to render the protein soluble (Oaks, M. K., et al., *Cellular Immunology*, 201:144-153 (2000), herein incorporated by reference in its entirety), or fragments and derivatives thereof. "Soluble CTLA4 molecules" also include fragments, portions or derivatives thereof, and soluble CTLA4 mutant molecules, having CTLA4 binding activity. The soluble CTLA4 molecules used in the methods of the invention may or may not include a signal (leader) peptide sequence. Typically, in the methods, compositions and/or its of the invention, the molecules do not include a signal peptide sequence.

As used herein "the extracellular domain of CTLA4" is the portion of CTLA4 that recognizes and binds CTLA4 ligands, such as B7 molecules. For example, an extracellular domain of CTLA4 comprises methionine at position +1 to aspartic acid at position +124 (FIG. 7). Alternatively, an extracellular domain of CTLA4 comprises alanine at position −1 to aspartic acid at position +124 (FIG. 7). The extracellular domain includes fragments or derivatives of CTLA4 that bind a B7 molecule. The extracellular domain of CTLA4 as shown in FIG. 7 may also include mutations that change the binding avidity of the CTLA4 molecule for a B7 molecule.

As used herein, a "CTLA4 mutant molecule" means wild-type CTLA4 as shown in (FIG. 7) or any portion or derivative thereof, that has a mutation or multiple mutations (preferably in the extracellular domain of wildtype CTLA4). A CTLA4 mutant molecule has a sequence that it is similar but not identical to the sequence of wild type CTLA4 molecule, but still binds a B7. The mutations may include one or more amino acid residues substituted with an amino acid having conservative (e.g., substitute a leucine with an isoleucine) or non-conservative (e.g., substitute a glycine with a tryptophan) structure or chemical properties, amino acid deletions, additions, frameshifts, or truncations. CTLA4 mutant molecules may include a non-CTLA4 molecule therein or attached thereto. The mutant molecules may be soluble (i.e., circulating) or bound to a cell surface. Additional CTLA4 mutant molecules include those described in U.S. Patent Application Ser. Nos. 09/865,321, 60/214,065 and 60/287, 576; in U.S. Pat. Nos. 6,090,914 5,844,095 and 5,773,253; and as described by Peach, R. J., et al., in *J. Exp. Med.*, 180:2049-2058 (1994)). CTLA4 mutant molecules can be made synthetically or recombinantly.

As used herein, "L104EA29YIg" is a fusion protein that is a soluble CTLA4 mutant molecule comprising an extracellular domain of wildtype CTLA4 starting at methionine at position +1 and ending at aspartic acid at position +124; or starting at alanine at position −1 to aspartic acid at position +124; a junction amino acid residue glutamine at position +125; and an immunoglobulin portion encompassing glutamic acid at position +126 through lysine at position +357 or glycine at position +356 with amino acid changes A29Y (a tyrosine amino acid residue substituting for an alanine at position 29) and L104E (a glutamic acid amino acid residue substituting for a leucine at position +104), or a portion thereof that binds a B7 molecule, joined to an Ig tail (FIG. 8). DNA encoding L104EA29YIg was deposited on Jun. 20, 2000 with ATCC number PTA-2104; copending in U.S. Patent Application Ser. Nos. 09/579,927, 60/287,576 and 60/214,065, incorporated by reference herein). The L104EA29YIg molecules may or may not include a signal (leader) peptide sequence.

As used herein, "treat" or "treating" a disorder or disease means to manage a disease or disorder by medicinal or other therapies. Treatment of a disease or disorder may suppress immune-mediated events associated with a disease, ameliorate the symptoms of a disease or disorder, reduce the severity of a disease or disorder, alter the course of disease or disorder progression and/or ameliorate or cure the basic disease or disorder problem. For example, to treat an immune system disease may be accomplished by regulating an immune response e.g., by regulating functional CTLA4- and/or CD28-positive cell interactions with B7-positive cells. Alternatively, treating an immune disease or disorder may be accomplished by preventing or inhibiting the disease or disorder from occurring or progressing through the use of the compositions described herein.

As used herein, "immune system disease" includes any disease mediated by T-cell interactions with B7-positive cells including, but not limited to, autoimmune diseases, immunoproliferative diseases, and immune disorders associated with graft transplantation.

As used herein, "immune disorders associated with graft transplantation" means any transplant related disease mediated by T-cell interactions with B7-positive cells including, but not limited to, immune disorders associated with graft transplantation rejection, graft related disorders, graft versus host disease (GVHD) (e.g., such as may result from bone marrow transplantation, or in the induction of tolerance), rejection of the graft or transplant including acute rejection of the graft or transplant and chronic rejection of the graft or transplant. The graft may be solid organ allografts or xenografts, tissue or cell allografts or xenografts or external anatomy allografts or xenografts, including but not limited to skin, islet cells (also known as islets), muscles, hepatocytes, neurons, heart, liver, kidney, lung, appendages, limbs, nose, ear or face.

As used herein, immunoproliferative diseases include, but are not limited to, T cell lymphoma; T cell acute lymphoblastic leukemia; testicular angiocentric T cell lymphoma; and benign lymphocytic angiitis.

As used herein autoimmune diseases include, but are not limited to diseases such as lupus (e.g., systemic lupus erythematosus(SLE), lupus nephritis), psoriasis; Hashimoto's thyroiditis, primary myxedema, Graves' disease, pernicious anemia, autoimmune atrophic gastritis, Addison's disease, diabetes (e.g., insulin dependent diabetes mellitus, type I diabetes mellitus, type II diabetes mellitus), good pasture's syndrome, myasthenia gravis, pemphigus, Crohn's disease, inflamatory bowel disease (IBD), sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, rheumatic diseases (e.g., rheumatoid arthritis, psoriatic arthritis), polymyositis, scleroderma, vasculitis (e.g., giant cell arteritis, polymyalgia rheumatica) and mixed connective tissue disease.

As used herein, "rheumatic diseases" means any disease that affects the joints, bone, soft tissue, or spinal cord (Mathies, H., *Rheuma* (1983)) and comprises inflammatory rheumatism, degenerative rheumatism, extra-articular rheumatism, and collagen diseases. Additionally, rheumatic diseases include, but are not limited to, chronic polyarthritis, psoriasis arthropathica, ankylosing spondylitis, rheumatoid arthritis, psoriatic arthritis, panarteriitis nodosa, systemic lupus erythematosus(SLE), progressive systemic scleroderma, periarthritis humeroscapularis, arthritis uratica, chondrocalcinosis, dermatomyositis, muscular rheumatism, myositis, and myogelosis. Some rheumatic diseases are known to be autoimmune diseases caused by a subject's altered immune response.

As used herein, "vaccine" refers to any preparation used as a preventive inoculation to confer immunity against a specific disease. A vaccine may be an innocuous form of the disease agent, such as a killed or weakened bacteria or virus, which stimulates antibody production. Inactivated vaccines are previously virulent microorganisms that have been killed with chemicals or heat. Examples of inactivated vaccines include vaccines against influenza (flu), cholera, bubonic plague and hepatitis A. Most inactivated vaccines may have incomplete or short-lived immune responses and are likely to require booster shots. Serious influenza in humans is caused by strains of several A subtypes (which are designated by the specific combination of the 19 hemagglutinin and 9 neuraminidase proteins, or antigens, found on the virus's surface, e.g., H1N1) and by strains of type B. The influenza vaccine confers immunity only to a particular strain, and immunity to one strain or subtype does not prevent susceptibility to another. Because the surface antigens of flu viruses change over time, it is necessary to reformulate the vaccine yearly in an educated guess at what strain will appear.

Live, attenuated vaccines are live microorganisms that have been cultivated under conditions which disable their virulent properties. They typically provoke more durable immunological responses and are the preferred type for healthy individuals. Examples of live attenuated vaccines include yellow fever, measles, rubella and mumps. Toxoids are inactivated toxic compounds produced by microorganisms that cause illness. Examples of toxoid-based vaccines include tetanus and diphtheria. Spores of *C. tetani* are ubiquitous. Serologic tests indicate that naturally acquired immunity to tetanus toxin does not occur in the US. Thus, universal primary vaccination with tetanus toxoid, with subsequent maintenance of adequate antitoxin levels by means of appropriately timed boosters, is necessary to protect persons among all age-groups. Tetanus toxoid vaccine consists of a formalin-inactivated tetanus toxin that is a highly effective antigen. A completed primary immunization series generally induces protective levels of neutralizing antibodies to tetanus toxin that persist for $\geq 10$ years.

Optionally, rather than introducing a whole inactivated or attenuated microorganism to an immune system, a fragment of the microorganism can create an immune response. An example is a vaccine that is composed of highly purified capsular polysaccharides from the 23 most prevalent or invasive pneumococcal types of *Streptococcus pneumoniae*, including the six serotypes (Danish 6B, 9V, 14, 19F, 19A, 23F) that most frequently cause invasive drug-resistant pneumococcal infections among children and adults in the United States.

Vaccines useful in the method of the instant invention include but are not limited to pneumococcal vaccine (such as Pneumovax® 23, Merck& Co), influenza vaccine (flu shot) and tetanus toxoid vaccine (such as Tetanus Toxoid Adsorbed USP, Aventis Pasteur, Inc). A vaccination is the act or practice of vaccinating (e.g., inoculation with a vaccine).

As used herein, a positive immune response is defined as having at least a two-fold increase in baseline levels of specific antibodies of interest.

In order that the invention herein described may be more fully understood, the following description is set forth.

Compositions and Methods of the Invention

The present invention relates to methods of vaccinating subjects receiving immune modulating therapy, such as soluble CTLA4 molecules for treatment of immune system diseases mediated by T-cell interactions with B7-positive cells including, but not limited to, autoimmune diseases, immunoproliferative diseases, and immune disorders associated with graft transplantation.

The health car provider will balance the vaccination timing against effective target trough levels of soluble CTLA4 molecules and the amount of time between the vaccination and the soluble CTLA4 molecules dose. The higher serum level of a soluble CTLA4 molecule the greater the suppression of the response to the vaccine. The amount of time between the vaccination and the soluble CTLA4 molecule dose determines how much time the B cells have to respond to the vaccination and complete their differentiation into antibody-secreting plasma cells before the soluble CTLA4 molecules dose diminishes the response to the vaccine. Therefore the optimum vaccination timing is a combination of effective soluble CTLA4 molecules serum level and time prior to the soluble CTLA4 molecules dose. Consequently the soluble CTLA4 molecule serum level may or may not be at the lowest effective level.

One embodiment of the invention comprises administering a vaccine to a subject being treated with a soluble CTLA4 molecule at a time when the serum trough level of the soluble CTLA4 molecule is at an effective level but lower than the serum level on the day of the soluble CTLA4 molecule administration.

Another embodiment of the invention comprises administering a vaccine to a subject being treated with a soluble CTLA4 molecule 14±3 days prior to the administration of the soluble CTLA4 molecule dose.

Another embodiment of the invention comprises administering a vaccine to a subject being treated with a soluble CTLA4 molecule 14±3 days after the administration of the soluble CTLA4 molecule dose.

Another embodiment of the invention comprises administering a vaccine to a subject being treated with a soluble CTLA4 molecule 7±3 days prior to the administration of the soluble CTLA4 molecule dose.

Another embodiment of the invention comprises administering a vaccine to a subject being treated with a soluble CTLA4 molecule at least 4 days prior to the administration of the soluble CTLA4 molecule dose.

In another embodiment of the invention comprises administering a vaccine to a subject being treated with a soluble CTLA4 molecule, wherein the soluble CTLA4 molecule is administered on a monthly basis.

Another embodiment of the invention comprises administering a vaccine to a subject being treated with a soluble CTLA4 molecule (i.e. concurrently with CTLA4 therapy) but wherein the vaccination and the soluble CTLA4 molecule are not necessarily dosed at the same time or on the same day. The vaccination and soluble CTLA4 molecules need not be an admixture. Subjects being treated with a soluble CTLA4 molecule may be in need of a vaccination. Subjects may have immune system diseases such as rheumatoid diseases and immune disorders associated with graft transplantation rejection.

Formulations comprising soluble CTLA4 molecules are described in copending U.S. Patent Application 60/752,149 and is hereby incorporated by reference into this application. As described in copending U.S. Patent Application 60/752, 149, soluble CTLA4 molecules may be formulated for IV and subcutaneous applications. Briefly, a suitable subcutaneous (SC) formulation comprises soluble CTLA4 molecules at a protein concentration of at least 100 mg/ml in combination with a sugar at stabilizing levels in an aqueous carrier.

An example of a CTLA4Ig SC drug product that is delivered via a pre-filed syringe is provided in Table 1 below.

TABLE 1

Composition of CTLA4Ig SC drug product, 125 mg/ml (125 mg/syringe)

| Component | Amount (mg/syringe) |
| --- | --- |
| CTLA4Ig | 125 |
| Sucrose | 170 |
| Poloxamer 188 | 8.0 |
| Sodium phosphate monobasic, monohydrate | 0.143 |
| Sodium phosphate dibasic, anhydrous | 0.971 |
| Water for Injection | q.s. to 1. ml |

An example of a suitable liquid formulation for IV comprises L104EA29YIg molecule at a protein concentration of at least 20 mg/ml in combination with a sugar at stabilizing levels in an aqueous carrier. A typical composition of L104EA29YIg liquid drug product, 20 mg/ml (250 mg/vial) is provided in Table 2 below.

TABLE 2

Composition of L104EA29YIg liquid drug product, 20 mg/ml (250 mg/vial)

| Component | Amount$^a$ (mg/vial) |
| --- | --- |
| L104EA29YIg | 260 |
| Sucrose | 520 |
| Sodium phosphate monobasic, monohydrate | 18.1 |
| Sodium chloride | 15.3 |
| Hydrochloric acid | Adjust to pH 7.5 |
| Sodium hydroxide | Adjust to pH 7.5 |
| Water for Injection | q.s. to 13 ml |

$^a$includes 4% overfill for vial, needle and syringe losses

An example of the CTLA4Ig lyophilized formulation utilized in Example 1 and Example 2 is listed in Table 3 below.

TABLE 3

Composition of lyophilized CTLA4Ig (250 mg/vial) drug product

| Component | Amount (mg/vial)$^a$ |
| --- | --- |
| CTLA4Ig | 262.5 |
| Maltose monohydrate | 525 |
| Sodium phosphate monobasic, monohydrate$^b$ | 18.1 |
| Sodium chloride$^b$ | 15.3 |
| Hydrochloric Acid | Adjust to pH 7.5 |
| Sodium hydroxide | Adjust to pH 7.5 |

$^a$includes a 5% overfill for vial, needle, syringe loss
$^b$These components are present in the CTLA4Ig drug substance solution The lyophilized CTLA4Ig drug product is constituted to about 25 mg/ml with 10 ml of either Sterile Water for Injection, USP (SWFI) or 0.9% Sodium Chloride Injection, USP. The constituted solution is further diluted to drug product concentrations between 1 and 10 mg/ml with 0.9% Sodium Chloride Injection, USP. The diluted drug product for injection is isotonic and suitable for administration by intravenous infusion.

Another embodiment of the invention comprises a method of treating a subject having immune system diseases comprising administering an effective dose of soluble CTLA4 molecules and administering a vaccine. Methods for treating immune system diseases by administering to a subject an effective amount of soluble CTLA4 molecules are described in copending U.S. patent applications Ser. Nos. 09/898,195, 10/419,008 and 11/399,666 and are hereby incorporated by reference into this application The most effective mode of administration and dosage regimen for an agent depends upon the severity and course of the disease, the patient's health and response to treatment and the judgment of the treating physician. Accordingly, the dosages (also known as doses) of the compositions should be titrated to the individual patient. For example, the effective target trough serum concentrations of soluble CTLA4 molecules disclosed herein to treat an immune system disease may be between about 0.2 µg/mL and about 70 µg/mL. Alternatively, the soluble CTLA4 molecules disclosed herein may be administered in an amount between about 0.1 to about 20.0 mg/kg weight of the patient to treat immune system diseases.

Another embodiment of the invention comprises a method for treating subjects having rheumatic disease comprising administering an effective dose of CTLA4Ig and administering a vaccine. As described in copending U.S. patent applications Ser. Nos. 09/898,195, 10/419,008 and 11/399,666, examples of an effective amount of a CTLA4Ig molecule useful to treat rheumatoid arthritis (RA) include 2 mg/kg weight of a subject and 10 mg/kg weight of a subject. Alternatively, an effective amount of a CTLA4Ig molecule useful to treat RA is 500 mg for a subject weighing less than 60 kg, 750 mg for a subject weighing between 60-100 kg and 1000 mg for a subject weighing more than 100 kg.

Doses of CTLA4Ig and administration regimens for treatment of RA may be dictated by the target serum trough profiles. The target trough serum concentration of CTLA4Ig in RA patients is between 1 µg/mL and 70 µg/mL, preferably between 5 µg/mL and 35 µg/mL, more preferably about 24 µg/mL. The half-life of CTLA4Ig in RA patients is between 8 and 25 days, preferably between 11 and 18 days, more preferably about 13 days.

Another embodiment of the invention comprises a method for treating immune disorders associated with graft transplantation rejection comprising administering to a subject an effective dose of L104EA29YIg and administering a vaccine. An example of an effective amount of a L104EA29YIg molecule useful to treat immune disorders associated with graft transplantation is 10 mg/kg weight of a subject during the early phase, in which doses are higher and the frequency of administration is increased during the period of greatest immunologic risk, followed by a maintenance phase where the dose is decreased to 5 mg/kg weight of a subject.

Doses of L104EA29YIg and administration regimens for treatment of immune disorders associated with graft transplantation may be dictated by the target serum trough profiles. As described in copending U.S. patent application Ser. No. 11/399,666, target trough serum concentration of L104EA29YIg between about 3 µg/mL and about 30 µg/mL over the first 3 to 6 months post-transplant will be sufficient to maintain function of the allograft, preferably between about 5 µg/mL and about 20 µg/mL. Target trough serum concentration of L104EA29YIg during the maintenance phase are between about 0.2 µg/mL and about 3 µg/mL, preferably between about 0.25 µg/mL and about 2.5 µg/mL.

The soluble CTLA4 molecules may be administered to a subject in an amount, at a frequency over a period of a time (e.g., length of time and/or multiple times) sufficient to block endogenous B7 (e.g., CD80 and/or CD86) molecules from binding their respective ligands, in the subject. Blockage of endogenous B7/ligand binding thereby inhibits interactions between B7-positive cells (e.g., CD80- and/or CD86-positive cells) with CD28- and/or CTLA4-positive cells. An effective amount of the molecule that blocks B7 interaction with CTLA4 and/or CD28 may be administered to a subject daily, weekly, monthly and/or yearly, in single or multiple times per hour/day/week/month/year, depending on need.

As described in copending U.S. patent applications Ser. Nos. 09/898,195, 10/419,008 and 11/399,666, the administration schedule for CTLA4Ig in the treatment of RA may initially be administered once every two weeks for a month, and then once every month thereafter. In an example of an administration schedule for L104EA29YIg in the treatment of immune disorders associated with graft transplantation, the early phase may range from the first 3 to 6 months post-transplantation. The administration regimen during early phase may vary depending on the status of the recipient and/or graft. For example, a more intensive early phase regimen would administer a higher dose of the molecules or the pharmaceutical compositions of the invention on day 1, day 5, week 2 visit (e.g., day 13-17), then every two weeks for the first 3 months (e.g., on week 4 visit, week 6 visit, week 8 visit, week 10 visit, and week 12 visit), followed by monthly administration through month 6 visit (e.g., on month 4 visit, month 5 visit, and month 6 visit). An example of a typical more intensive early phase regimen is administration of 10 mg/kg weight of the patient of L104EA29YIg at daysl, 5, 15, 29, 43, 57, 71, 85, 113, 141 and 169. A less intensive regimen, for example, would administer the molecules or the pharmaceutical compositions of the invention on day 1, week 2 visit, week 4 visit, then monthly through month 3 visit. An example of a typical less intensive early phase regimen is administration of 10 mg/kg weight of the patient of L104EA29YIg on days1, 15, 29, 57 and 85. The early phase is followed by a maintenance phase where lower doses of the L104EA29YIg molecule is administered at one to two month intervals for as long as needed, typically for as long as the patient retains the transplant. An example of the maintenance phase for the more intensive regimen described above includes monthly administration of 5 mg/kg weight of the patient of L104EA29YIg starting at month 7 visit. While an example of the maintenance phase for the less intensive regimen above would include monthly administration of 5 mg/kg weight of the patient of L104EA29YIg starting at month 4 visit. Alternatively, one knowledgeable in the art would be able to modify this administration regimen in response to the patients risk status and/or response to the therapy post transplantation. For example, the early phase of the less intensive regimen described above could be modified by adding administration day 5 to the regimen, thereby increasing the frequency of administration during the period of greatest immunologic risk. As used herein, "four weeks," "month", "months" or "monthly" refers to a period of 28±5 days. As used herein, "two weeks" refers to a period of 14±3 days. As used herein, day 1 is defined as the day of the transplant or the first day of treatment with L104EA29YIg molecules.

Example 1 describes the effect of a single, intravenous (IV) 750 mg dose of CTLA4Ig on the antibody response to both tetanus toxoid and 23-valent pneumococcal vaccines in healthy subjects who 1) received injections of tetanus toxoid and 23-valent pneumococcal vaccines 13 days (2 weeks) prior to a single IV dose of CTLA4Ig; 2) received injections of tetanus toxoid and 23-valent pneumococcal vaccines 13 days (2 weeks) after a single IV dose of CTLA4Ig; 3) received injections of tetanus toxoid and 23-valent pneumococcal vaccines 55 days (8 weeks) after a single IV dose of CTLA4Ig.

A lowered response, as measured by antibody titers, was noted in subjects who were vaccinated after CTLA4Ig administration (vaccine 2 and 8 Weeks post-CTLA4Ig). However, CTLA4Ig did not inhibit the ability of healthy adults to mount a positive ($\geq$2-fold) response to tetanus toxoid or pneumococcal vaccine. Patients vaccinated prior to CTLA4Ig treatment generated the most favorable antibody responses to vaccination. Clearly, there is a relationship between serum levels of CTLA4Ig present at the time of vaccination and the degree of inhibition of the humoral response.

The assay to quantify IgG anti-tetanus toxoid levels was based on the methodology described in Manghi M, Pasetti M, Brero M, et al. Development of an ELISA for measuring the activity of tetanus toxoid in vaccines and comparison with the toxin neutralization test in mice. *J. Immunol. Methods.*, 168 (1):27-24 (1994). The assay to quantify IgG anti-pneumococcal antibody levels was based on the Procedures of the World Health Organization Pneumococcal Serology Reference Laboratories at the Institute of Child Health, University College, London, England, and Wernette, C. M., Frasch, C. E., Madore, D., et al., Enzyme-linked immunosorbent assay for quantitation of human antibodies to pneumococcal polysaccharides, *Clin. Diagn. Lab Immunol.*, 10(4):514-519 (2003).

The assay to quantify soluble CTLA4 molecules in human serum comprises an enzyme immunoassay (EIA).

In another embodiment of the invention, the vaccine is administered at a time when the serum level of soluble CTLA4 molecule is low but remains in the effective serum trough range. Identifying the time of low serum CTLA4 molecules becomes a challenge when the subject, for example, with rheumatoid arthritis or a subject having received a transplant, is receiving therapies comprising an administration regime of soluble CTLA4 molecules based on the administrating schedules described above. The health care provider would have to balance the vaccination timing against effective target serum trough levels for the CTLA4 molecules. For example, Example 2 describes an experiment designed to evaluate whether RA patients on a stable DMARD therapy, can mount a positive response to pneumococcal vaccination as assessed by a two-fold increase in post-immunization titers to pneumovax immunization. Subjects receiving monthly infusions of CTLA4Ig will receive an immunization with 0.5 mL Pneumovax® 23 vaccine 7±3 days prior to their next regularly scheduled CTLA4Ig infusion. Subjects will then return for their regularly scheduled CTLA4Ig infusion. At the subjects subsequent infusion date (28 days later), immediately prior to the CTLA4Ig infusion, the subject will have blood sample drawn to determine the response to the pneumovax immunization as assessed by determining titers to the relevant pneumococcal serotypes.

EXAMPLES

The following examples are presented to illustrate the present invention and to assist one of ordinary skill in making and using the same. The examples are not intended in any way to otherwise limit the scope of the invention.

Example 1

The effect of CTLA4Ig on response to therapeutic vaccines has not been previously evaluated. Reported here are the results of a study to evaluate the effects of CTLA4Ig on the antibody response following tetanus toxoid and 23-valent pneumococcal vaccinations in healthy subjects.

Materials and Methods

Healthy men and women aged 18 to 65 years who weighed between 60 and 100 kg were eligible for the study. The health of study subjects was determined by the absence of clinically significant deviation from normal in medical history, physical examination, clinical laboratory determinations and electrocardiograms. Women of childbearing potential had to have a negative pregnancy test within the 48 hours prior to the start of the study and had to use an adequate method of contraception to avoid pregnancy throughout the study and for up to 10 weeks after dosing of CTLA4Ig. Women were also required to have age and/or risk-factor appropriate breast cancer screening prior to entry into the study. Male subjects had to use an adequate method of contraception throughout the study and for up to 10 weeks after dosing of CTLA4Ig. Subjects with a known or suspected autoimmune or immunodeficiency disorder, recent infection requiring antibiotic treatment, serum anti-tetanus antibodies below the clinically reportable range (<0.1 IU/mL), vaccination with tetanus (including tetanus booster) or 23-valent pneumococcal vaccine within 5 years of enrollment, history of severe local or systemic reaction or hypersensitivity to tetanus or pneumococcal vaccines, history of anaphylaxis, asthma or allergies, or a history of any significant drug allergy were excluded. Prohibited therapies and medications included prior exposure to CTLA4Ig, use of prescription drugs during the 4 weeks prior to study enrollment (with the exception of hormone replacement therapy or medications designed to prevent pregnancy), use of other drugs including over-the-counter medications and herbal preparations within the week prior to enrollment, administration of oral polio vaccine or exposure to household contact during the course of the study, and any live vaccination in the 4 weeks prior to enrollment.

Study Design

This open label, parallel group, controlled study was conducted at three study centers in the United States. Subjects were randomized to one of four treatment groups; Vaccine/Control (subjects received separate 0.5 mL intramuscular (IM) injections of tetanus toxoid and 23-valent pneumococcal vaccines on Day 1 without CTLA4Tg ); Vaccine Pre-CTLA4Ig (subjects received separate 0.5 mL IM injections of tetanus toxoid and 23-valent pneumococcal vaccines on Day 1 followed 13 days later by a single intravenous (IV) dose of 750 mg CTLA4Ig); Vaccine 2 Weeks Post-CTLA4Ig (subjects received a single IV dose of 750 mg CTLA4Tg on Day 1 followed 13 days later by separate 0.5 mL IM injections of tetanus toxoid and 23-valent pneumococcal vaccines); Vaccine 8 Weeks Post-CTLA4Tg (subjects received a single IV dose of 750 mg abatacept on Day 1 followed 55 days later by separate 0.5 mL IM injections of tetanus toxoid and 23-valent pneumococcal vaccines) (FIG. 1). Randomization was done by a computer-generated randomization scheme. Randomization numbers were assigned in order of enrollment. Subjects were not replaced if they discontinued the study.

CTLA4Tg (Abatacept, Bristol Myers Squibb, Princeton N.J.) 750 mg was administered to subjects randomized to receive the active CTLA4Tg treatment by IV over 30 minutes using a calibrated, constant-rate infusion. Tetanus toxoid vaccine (Aventis Pasteur Inc, Swiftwater, Pa.) and 23-valent pneumococcal vaccines (Merck & Co, Inc, Whitehouse Station, N.J.) were administered separately via IM injection in either the deltoid or the lateral mid-thigh.

Study Objectives

The primary objective of the study was to assess the effect of a single, IV 750 mg dose of CTLA4Ig on the antibody response to both tetanus toxoid and 23-valent pneumococcal vaccines in healthy subjects. The secondary objective was to assess the safety and tolerability of CTLA4Ig given in conjunction with both vaccines.

Safety and Tolerability

Safety assessments were based on medical reviews of AEs, physical examinations, vital signs, and clinical laboratory results. Adverse events included those volunteered by the subjects and those elicited by study staff and were defined as any untoward medical occurrence (including worsening of a new medical occurrence), or worsening of a pre-existing medical condition in a subject administered a medicinal product and which did not necessarily have a causal relationship with the medicinal product. The incidence of AEs was tabulated by system organ class and reviewed for clinical significance. All identified AEs were recorded and described by the investigators. Treatment-emergent AEs included those that occurred during and after treatment with CTLA4Ig, including those that occurred during the 30-day period following study discharge. Subjects were also contacted between 24 and 48 hours after the CTLA4Ig infusion for documentation of any peri-infusional AEs, defined as any AE occurring within the 24-hour period after the start of the CTLA4Ig infusion.

Pharmacodynamics

The results of vaccination with tetanus toxoid and 23-valent pneumococcal vaccines are expressed as absolute titers of antibodies. Seven serotypes of 23-valent pneumococcal vaccines were chosen as a representative sample of differing immunogenic strengths of pneumococcal vaccine. A two-fold or higher increase above baseline levels of specific antibodies was considered a positive immune response against tetanus toxoid and against each of the seven serotypes of the 23-valent pneumococcal vaccine. Anti-tetanus antibody and anti-pneumococcal antibodies (Danish types 2, 6B, 8, 9V, 14, 19F, and 23 F) were collected by blood sample and measured 14 days and 28 days after vaccinations. CTLA4Ig serum concentrations were measured at the same time antibody titers were drawn. Pharmacodynamic activity of CTLA4Ig was derived from an assessment of antibody levels. Subjects who were randomized to receive vaccines two weeks before CTLA4Ig administration had their blood sample collected for antibody determinations prior to the start of the CTLA4Ig infusion on Day 14 (Vaccine Pre-CTLA4Ig group).

For determination of anti-tetanus and anti-pneumococcal antibody levels, a 10 mL blood sample was collected, allowed to clot and the serum was separated. Serum samples were frozen and shipped to the analytical facility for analysis. The assay to quantify IgG anti-tetanus toxoid levels was based on the methodology described in Manghi, M., Pasetti, M., Brero, M., et al., Development of an ELISA for measuring the activity of tetanus toxoid in vaccines and comparison with the toxin neutralization test in mice, *J. Immunol. Methods.*, 168 (1):27-24 (1994). The assay to quantify IgG anti-pneumococcal antibody levels was based on the Procedures of the World Health Organization Pneumococcal Serology Reference Laboratories at the Institute of Child Health, University College, London, England, and Wernette C. M., Frasch, C. E., Madore, D., et al., Enzyme-linked immunosorbent assay for quantitation of human antibodies to pneumococcal polysaccharides, *Clin. Diagn. Lab Immunol.*, 10(4):514-519 (2003).

Statistical Methods

The number of subjects was not based on statistical considerations. Despite this, 15 subjects per treatment group provided 95% confidence that the estimates of the ratio of geometric means (post-vaccination/baseline) in each treatment group were within 141% of the true value for the anti-tetanus-IgG (Ttox-IgG). Additionally, 15 subjects per treatment group provided 95% confidence that the estimates of the ratio of geometric means (post-vaccination/baseline) within each treatment group were within 40% to 91% of the true values for the anti-pneumococcal antibody Danish types assessed. The calculations assumed that the antibody concentrations were log normally distributed with a standard deviation of 1.51 for the anti-tetanus antibodies and intersubject standard deviations ranging from 0.697 to 1.192 for the anti-pneumococcal antibodies.

Results

Eighty study subjects were enrolled and randomized to a treatment group. Of these, 77 (96%) completed treatment and three (4%) discontinued early from the study.

Reasons for study discontinuation included upper respiratory infection (n=1; Vaccine Pre-CTLA4Ig group) and subjects no longer meeting study criteria because of positive toxicology screens (n=2, one each: Vaccine 2 Weeks Post-CTLA4Ig group and Vaccine 8 Weeks Post-CTLA4Ig group). Serum CTLA4Ig samples for three subjects in the Vaccine 2 Weeks Post-CTLA4Ig group were not collected on Day 14 prior to vaccines due to staff error. One patient's serum concentrations of CTLA4Ig collected prior to CTLA4Ig administration and 30 minutes after administration were not included in the calculation of the summary statistics of CTLA4Ig serum concentrations by treatment group because the concentrations appeared to be reversed and the deviation could not be confirmed. Antibody determinations for one patient in the Vaccine 8 Weeks Post-CTLA4Ig group and one patient in the Vaccine 2 Weeks Post-CTLA4Ig group were not included in the statistical analysis because the patient terminated participation in the study prior to vaccine administration on Days 56 and Day 14, respectively.

Baseline Demographics and Clinical Characteristics

Baseline demographic and clinical characteristics were similar in the four groups (Table 4). None of the medical history findings and presenting conditions reported by the study participants had any effect on the outcome of the study.

TABLE 4

| | Demographic Characteristics | | | |
|---|---|---|---|---|
| Characteristic | Treatment A [a] N = 20 | Treatment B [a] N = 20 | Treatment C [a] N = 20 | Treatment D [a] N = 20 |
| Age, years | | | | |
| Mean | 34 | 34 | 34 | 36 |
| SD | 12 | 13 | 11 | 13 |
| Range | 18-55 | 18-56 | 19-56 | 20-55 |
| Gender, n (%) | | | | |
| Male | 10 (50) | 8 (40) | 10 (50) | 11 (55) |
| Female | 10 (50) | 12 (60) | 10 (50) | 9 (45) |
| Race, n (%) | | | | |
| White | 15 (75) | 12 (60) | 14 (70) | 11 (55) |
| Black | 5 (25) | 8 (40) | 6 (30) | 8 (40) |
| Other | 0 | 0 | 0 | 1 (5) |
| Ethnicity n (%) | | | | |
| Not Hispanic/Latino | 17 (85) | 18 (90) | 19 (95) | 19 (95) |
| Hispanic/Latino | 3 (15) | 2 (10) | 1 (5) | 1 (5) |
| Weight, kg | | | | |
| Mean | 81.8 | 75.4 | 75.5 | 76.8 |
| SD | 12.0 | 9.0 | 11.8 | 11.5 |
| Range | 65.4-99.0 | 62.4-89.4 | 60.6-96.6 | 59.1-98.1 |
| Height, cm | | | | |
| Mean | 173.4 | 169.5 | 171.7 | 172.6 |
| SD | 9.3 | 8.4 | 8.2 | 9.0 |
| Range | 162.0-193.0 | 158.0-187.0 | 155.3-188.3 | 154.0-186.0 |

[a] A = Vaccines alone on Day 1; B = Vaccines on Day 1, CTLA4Ig on Day 14; C = CTLA4Ig on Day 1, vaccines on Day 14; D = CTLA4Ig on Day 1, vaccines on Day 56;

Antibody Response to Tetanus Toxoid

Intersubject variability in response to tetanus toxoid was large with percentage coefficient of variation ranging between 54% and 112% (Table 5). Based on the geometric mean of the antibody titers, there was a lowered response of approximately 48% and 21% at Day 14 and Day 28, respectively, after vaccination in subjects in the Vaccine 2 Weeks Post-CTLA4Ig group, and to a lesser extent (~39% and 26% at Day 14 and Day 28, respectively, after vaccination) in subjects in the Vaccine 8 Weeks Post-CTLA4Ig group (Table 5).

TABLE 5

Geometric means (% CV) of antibody titers taken Day 14 and Day 28 after tetanus toxoid vaccination

| Group | N | Baseline Titers (U/mL) | Day 14 After Vaccination | | Day 28 After Vaccination | |
|---|---|---|---|---|---|---|
| | | | Antibody Titers (U/mL) | Abatacept Conc (μg/mL) | Antibody Titers (U/mL) | Abatacept Conc (μg/mL) |
| 1 | 20 | 1.6 (106) | 11.4 (88) | <LLQ | 9.3 (104) | <LLQ |
| 2 | 20 | 1.9 (76) | 10.2 (71) | <LLQ | 8.7 (68)* | 28.6 (26)* |
| 3 | 19 | 2.3 (76) | 5.9 (112) | 12.5 (19) | 5.6 (98) | 6.1 (20) |
| 4 | 19 | 2.3 (54) | 9.0 (79) | 1.3 (56) | 7.8 (85) | 0.4 (106) |

*N = 19
1 = Vaccines alone on Day 1; 2 = Vaccines on Day 1, CTLA4Ig on Day 14; 3 = CTLA4Ig on Day 1, vaccines on Day 14; 4 = CTLA4Ig on Day 1, vaccines on Day 56;

Across all treatment groups, greater than 60% of subjects were able to generate a ≧2-fold increase in antibody response at Day 28. The percentage of subjects who mounted a response that was ≧2-fold from baseline is shown in FIG. 2. The responses observed at Day 14 and Day 28 after vaccination were similar.

Antibody Responses to 23-Valent Pneumococcal Vaccine

As with the response to tetanus toxoid, variable response rates were obtained in the study subjects across individual serotypes (Table 6).

TABLE 6

Geometric Mean (Percentage Coefficient of Variation) of Antibody Titers (IU/mL) Before and After Pneumococcal Vaccination and the Fold Increase from Baseline

| Treatment[a] | N | Baseline (μg/mL) | 14 Days Post-Vaccination (μg/mL) | Fold Increase[b] (95% CI) | 28 Days Post-Vaccination (μg/mL) | Fold Increase[b] (95 % CI) |
|---|---|---|---|---|---|---|
| Serotype 14 | | | | | | |
| A | 20 | 1.9 (112) | 20.5 (236) | 10.8 (5.6, 21.1) | 23.5 (199) | 12.4 (6.4, 24.1) |
| B | 20 | 1.9 (132) | 15.5 (105) | 8.3 (4.3, 16.1) | 15.4 (111)[c] | 7.9 (4.0, 15.4) |
| C | 19 | 1.8 (201) | 12.0 (195) | 6.8 (3.4, 13.4) | 12.8 (250) | 7.3 (3.7, 14.3) |
| D | 19 | 1.8 (125) | 18.0 (155) | 10.1 (5.1, 20.0) | 12.6 (141) | 7.0 (3.6, 13.9) |
| Serotype 2 | | | | | | |
| A | 20 | 1.0 (163) | 13.4 (113) | 13.7 (8.3, 22.9) | 15.4 (110) | 15.8 (9.5, 26.4) |
| B | 20 | 1.1 (84) | 12.3 (109) | 12.4 (7.5, 20.7) | 13.2 (107)[c] | 12.3[c] (7.4, 20.4) |
| C | 19 | 0.8 (90) | 4.1 (118) | 4.7 (2.8, 8.0) | 4.8 (115) | 5.5 (3.3, 9.3) |
| D | 19 | 0.7 (122) | 7.0 (132) | 9.4 (5.5, 15.8) | 7.7 (136) | 10.3 (6.1, 17.5) |
| Serotype 23F | | | | | | |
| A | 20 | 0.9 (101) | 3.0 (112) | 3.1 (2.0, 4.9) | 3.3 (113) | 3.3 (2.1, 5.2) |
| B | 20 | 1.8 (124) | 5.6 (87) | 3.4 (2.1, 5.3) | 4.9 (89)[c] | 3.1[c] (2.0, 4.8) |
| C | 19 | 1.2 (158) | 4.5 (112) | 3.7 (2.4, 5.9) | 5.1 (106) | 4.2 (2.7, 6.6) |
| D | 19 | 1.5 (125) | 6.2 (92) | 4.2 (2.7, 6.7) | 6.7 (90) | 4.6 (2.9, 7.3) |
| Serotype 8 | | | | | | |
| A | 20 | 1.5 (120) | 10.1 (138) | 6.4 (4.3, 9.5) | 9.6 (114) | 6.1 (4.1, 9.0) |
| B | 20 | 2.3 (104) | 12.0 (61) | 6.3 (4.2, 9.5) | 10.5 (81)[c] | 5.7[c] (3.8, 8.4) |
| C | 19 | 1.4 (104) | 4.0 (68) | 2.6 (1.7, 3.9) | 4.4 (64) | 2.8 (1.9, 4.3) |
| D | 19 | 1.6 (74) | 5.1 (144) | 3.2 (2.1, 4.7) | 5.2 (106) | 3.2 (2.2, 4.9) |
| Serotype 9V | | | | | | |
| A | 20 | 0.9 (148) | 6.1 (102) | 6.7 (4.2, 10.7) | 6.4 (99) | 7.1 (4.4, 11.3) |
| B | 20 | 1.3 (158) | 4.0 (97) | 3.4 (2.1, 5.45) | 3.9 (101)[c] | 3.2[c] (2.0, 5.1) |
| C | 19 | 0.9 (190) | 3.0 (147) | 3.2 (2.0, 5.2) | 3.2 (108) | 3.5 (2.2, 5.7) |
| D | 19 | 0.9 (119) | 2.0 (107) | 2.2 (1.4, 3.6) | 2.3 (106) | 2.5 (1.6, 4.1) |
| Serotype 19F | | | | | | |
| A | 20 | 5.3 (95) | 13.0 (125) | 2.4 (1.6, 3.7) | 13.9 (150) | 2.6 (1.7, 3.9) |
| B | 20 | 10.3 (127) | 19.9 (105) | 2.2 (1.4, 3.4) | 19.6 (97)[c] | 2.3[c] (1.5, 3.5) |

TABLE 6-continued

Geometric Mean (Percentage Coefficient of Variation) of Antibody Titers (IU/mL)
Before and After Pneumococcal Vaccination and the Fold Increase from Baseline

| Treatment[a] | N | Baseline (µg/mL) | 14 Days Post-Vaccination (µg/mL) | Fold Increase[b] (95% CI) | 28 Days Post-Vaccination (µg/mL) | Fold Increase[b] (95 % CI) |
|---|---|---|---|---|---|---|
| C | 19 | 4.3 (117) | 10.0 (178) | 2.2 (1.4, 3.3) | 10.3 (180) | 2.2 (1.4, 3.4) |
| D | 19 | 5.6 (75) | 9.9 (89) | 1.8 (1.1, 2.7) | 10.3 (88) | 1.8 (1.2, 2.8) |
| Serotype 6B | | | | | | |
| A | 20 | 1.6 (103) | 5.9 (197) | 3.5 (2.3, 5.3) | 6.1 (204) | 3.6 (2.4, 5.5) |
| B | 20 | 3.1 (126) | 7.8 (87) | 2.9 (1.9, 4.4) | 7.1 (95)[c] | 2.7[c] (1.8, 4.1) |
| C | 19 | 1.9 (140) | 4.6 (147) | 2.4 (1.5, 3.6) | 4.6 (141) | 2.4 (1.6, 3.6) |
| D | 19 | 1.8 (114) | 3.5 (159) | 1.9 (1.2, 2.9) | 3.5 (151) | 1.9 (1.2, 2.9) |

[a]A = Vaccines alone on Day 1; B = Vaccines on Day 1, CTLA4Ig on Day 14; C = CTLA4Ig on Day 1, vaccines on Day 14; D = CTLA4Ig on Day 1, vaccines on Day 56;
[b]Ratio of geometric means adjusted for baseline;
[c]N = 19

Lower titers were recorded for all serotypes, except 23F, in subjects who received vaccination after CTLA4Ig (Vaccine 2 Weeks Post-CTLA4Ig group and Vaccine 8 Weeks Post-CTLA4Ig group). The decrease in antibody response in subjects in the Vaccine 2 Weeks Post-CTLA4Ig group at Day 14 and Day 28 after vaccination ranged from 22% to 69% at Day 14 and 24% to 68% at Day 28. Similarly, the decrease in antibody response for subjects in the Vaccine 8 Weeks Post-CTLA4Ig group determined at Day 14 and Day 28 after vaccination ranged between 12% and 67% and between 25% and 64%, respectively. The percentage of subjects in all treatment groups achieving a positive response to the different serotypes on Day 14 and Day 28 after vaccination was similar (FIGS. 3 and 4).

A lowered vaccine response in subjects in the Vaccine Pre-CTLA4Ig group could not be accurately evaluated because of higher baseline values obtained in these subjects.

Safety and Tolerability

Overall, 59 AEs were reported for 29 (49.2%) subjects (Table 7). The most frequently reported AEs were nervous system disorders, predominately headache, reported by a total of 12 subjects (20.3%): four subjects in the Vaccine Pre-CTLA4Ig group, two subjects receiving Vaccine 2 Weeks Post-CTLA4Ig group, and six subjects in the Vaccine 8 Weeks Post-CTLA4Ig group. Seven out of 12 headaches were considered possibly related to CTLA4Ig.

TABLE 7

Number (Percentage) of Subjects with Treatment-emergent
Adverse Events, by System Organ Class and Preferred Term

| System Organ Class Preferred Term | Treatment B[a] (after abatacept) (N = 19) | Treatment C[a] (N = 20) | Treatment D[a] (N = 20) | Treatments B, C &D[a] (N = 59) |
|---|---|---|---|---|
| Breast Disorders | | | | |
| Menorrhagia | 1 (5.3) | 0 | 0 | 1 (1.7) |
| Menopausal symptoms | 0 | 1 (5.0) | 0 | 1 (1.7) |
| Skin and Subcutaneous Tissue Disorders | 1 (5.3) | 0 | 1 (5.0) | 2 (3.4) |
| Erythema | 1 (5.3) | 0 | 0 | 1 (1.7) |
| Pruritus generalized | 1 (5.3) | 0 | 0 | 1 (1.7) |
| Urticaria generalized | 0 | 0 | 1 (5.0) | 1 (1.7) |
| Ear and Labyrinth Disorders | 0 | 0 | 1 (5.0) | 1 (1.7) |
| Tympanic membrane disorder | 0 | 0 | 1 (5.0) | 1 (1.7) |
| Immune System Disorders | 0 | 0 | 1 (5.0) | 1 (1.7) |
| Anaphylactoid reaction | 0 | 0 | 1 (5.0) | 1 (1.7) |
| Investigations | 0 | 1 (5.0) | 0 | 1 (1.7) |
| White blood cell count decreased | 0 | 1 (5.0) | 0 | 1 (1.7) |
| Psychiatric Disorders | 0 | 0 | 1 (5.0) | 1 (1.7) |
| Restlessness | 0 | 0 | 1 (5.0) | 1 (1.7) |
| Total Events[b] | 16 | 16 | 27 | 59 |
| Total Subjects | 9 (47.4) | 7 (35.0) | 13 (65.0) | 29 (49.2) |

Over 70% of subjects responded to ≧3 different serotypes, and approximately 25% to 30% of subjects responded to ≧6 different serotypes by Day 14 (FIG. 5). Similar results were achieved at Day 28 after vaccination.

Discussion

As vaccinations are considered an essential component of routine health maintenance, it is important to evaluate the response to vaccination when the patient is receiving immunosuppressive therapy. In this single-dose, open-label study in healthy subjects, CTLA4Ig did not inhibit the ability of healthy subjects to develop a ≧2-fold response to either tetanus toxoid or a 23-valent pneumococcal vaccine. More than 60% of subjects included in the study were able to generate a positive response to the tetanus toxoid vaccine. In addition, approximately 25% to 30% of subjects in all treatment groups responded to ≧6 serotypes of the pneumococcal vaccine, an expected and normal response in healthy subjects.

A lowered response, as measured by antibody titers, was noted in subjects who were vaccinated after CTLA4Ig administration (vaccine 2 and 8 Weeks post-CTLA4Ig). However, CTLA4Ig did not inhibit the ability of healthy adults to mount a positive (≧2-fold) response to tetanus toxoid or pneumococcal vaccine. Data from this study suggest that patients vaccinated pre-CTLA4Ig treatment (vaccine pre-CTLA4Ig group), generated the most favorable antibody responses to vaccination. This could be attributed to the fact that CTLA4Ig was administered 2 Weeks after vaccination and so a pool of B cells that had completed their differentiation into antibody-secreting plasma cells was available. Conversely, subjects in the Vaccine 2 Weeks Post-CTLA4Ig (CTLA4Ig on Day 1, vaccines on Day 14), who presented with the highest levels of serum CTLA4Ig at the time of vaccination, had the lowest responses to vaccination. Subjects in the Vaccine 8 Weeks Post-CTLA4Ig (CTLA4Ig on Day 1, vaccine on Day 56), presented very low levels of serum CTLA4Ig at the time of vaccination and were less affected. These data suggest that the there is a relationship between serum levels of CTLA4Ig present at the time of vaccination and the degree of inhibition of the humoral response.

Conclusions

This study suggests that a single dose of CTLA4Ig does not inhibit the ability of healthy individuals to develop a positive response to tetanus toxoid or 23-valent pneumococcal vaccine. Although further studies will be necessary to confirm the optimal timing of vaccination, in this study, a single 750 mg IV dose of CTLA4Ig administered 2 weeks after tetanus toxoid and 23-valent pneumococcal vaccines appeared to be safe and well tolerated.

Example 2

Pneumovax vaccination is critical for Rheumatoid Arthritis (RA) patients, due to the high degree of morbidity and mortality of pneumonia in this patient population. As described in Example 1, healthy subjects who were vaccinated with pneumovax vaccine, were able to mount a positive response after a single dose of CTLA4Ig. However, there is no data available documenting whether patients on a stable DMARD therapy, can mount a positive response to pneumococcal vaccination. This study will provide critical data on whether RA patients can mount a positive response to a critical vaccination.

It is planned that approximately 30 subjects will participate in this study. Subjects who have consented to participate in this study and who voluntarily have given written informed consent will be brought in for a visit 7 days prior to their next regularly scheduled CTLA4Ig infusion. The subject's scheduled visit may take place within three days prior to or after the target day to adjust for the subject's and/or the sites personnel's convenience. At that visit they will have blood drawn (approximately 10 mLs) for CTLA4Ig trough levels and titers to the relevant pneumococcal serotypes. After the blood is drawn they will receive an immunization with 0.5 mL Pneumovax® 23 vaccine (Merck Laboratories) IM, according to manufacturer's instructions. All subjects are to be contacted between 24 and 48 hours after vaccine administration for adverse event monitoring.

Subjects will then return for their regularly scheduled CTLA4Ig infusion in 7 days. At the subjects next infusion date (28 days later), immediately prior to the infusion, the subject will have blood drawn (approximately 5 mLs) for titers to the relevant pneumococcal serotypes.

The primary objective of this study is to demonstrate that subjects with RA on a stable background DMARD therapy, will be able to mount a positive response to pneumovax immunization, as assessed by a two-fold increase in post-immunization titers to pneumovax immunization. The relevant serotypes that will be examined are 14, 19F, 2, 23F, 6B, 8, & 9V.

The subjects for this study will be recruited from an ongoing larger study that has been designed to assess the safety of CTLA4Ig in a clinical practice setting in subjects with active RA on background non-biologic DMARDs who have an inadequate response to anti-TNF therapy. The larger study is a 6-month open label study. Efficacy, tolerability and safety will be assessed throughout the duration of the study. The primary efficacy endpoint will be analyzed after subjects complete 6 months of treatment or discontinue therapy. The multinational, multicenter study utilizes an open-label design. It is anticipated that approximately 750 eligible subjects worldwide with active RA while on background non-biologic DMARDS will be administered study treatment. Subjects will receive open label CTLA4Ig intravenous infusion. Subjects will be dosed based on their screening visit weight. Subjects weighing <60 kg will receive 500 mg, subjects weighing 60 kg to 100 kg will receive 750 mg and subjects weighing >100 kg will receive 1 gram. Following the initial administration, CTLA4Tg should be given at 2 and 4 weeks after the first infusion, then once a month thereafter (i.e. Day 1, 15, 29, 57, 85, 113, 141). Each dose of study medication will be infused intravenously over approximately 30 minutes. One or more background non-biologic DMARDs will continue to be given to subjects during the study at the dose level(s) and regimen(s) administered at the time of treatment (Day 1). The definition of anti-TNF therapy inadequate response in RA includes 1) subjects with RA who are currently receiving or previously received an anti-TNF therapy at an approved labeled dose for at least 3 months, but had in the physician's opinion, an inadequate efficacy response to therapy and 2) subjects who discontinue or discontinued an anti-TNF therapy due to intolerance or safety. Subjects will be considered as anti-TNF therapy inadequate respondres at any time point after they have received their first dose of anti-TNF therapy. Men or women (not nursing and not pregnant) at least 18 years of age are eligible to participate. In addition, subjects must meet the criteria of the American Rheumatism Association for the diagnosis of rheumatoid arthritis and the American College of Rheumatology (ACR) functional classes I, II or III. Subjects must have RA for greater than 1 year from the time of the initial diagnosis of RA. Subjects with RA who are currently receiving or previously received an anti-TNF therapy at an approved labeled dose for at least 3 months of therapy (designated as anti-TNF therapy inadequate response) and with active RA disease activity will be considered. Subjects must have a qualifying DAS28≧5.1. Subjects who have a DAS28≧4.8 but <5.1 at screening, will be allowed to repeat the Tender and Swollen Joint Count and the subject's assessment of disease activity (VAS) in order to reassess eligibility. These assessments may be repeated only once and must be completed within 2 weeks of the initial screening visit. The hs-CRP component may not be repeated.

Safety assessments will be based on adverse event reports. All subjects who receive study medication (Pneumovax® 23 vaccine, (Merck Laboratories)) will be included in the safety evaluation. The incidence of adverse events will be tabulated and reviewed for potential significance and clinical importance.

Blood samples to quantify levels of CTLA4Ig will be collected immediately prior to vaccination. These samples will be obtained at the same time that samples are collected for antibody determinations in order to correlate the concentrations of CTLA4Ig with the antibody response to 23-valent pneumococcal vaccine.

A subject diagnosed with RA wishing to enter this study must be on a stable dose of CTLA4Ig, as defined by having received at least four infusions of CTLA4Ig. Subjects who have been vaccinated with 23-valent pneumococcal vaccine within 5 years of enrollment or if the subject is unsure as to whether or not he or she has received this vaccine within the previous 5 years are excluded from this study.

Pneumovax® 23 vaccine, 575 mcg/0.5 mL, will be administered to the sub-set of subjects according to the direction in the package inserts provided by Merck Laboratories. The vaccine should be given by intramuscular or subcutaneous injection (deltoid or lateral mid-thigh). All subjects are to be contacted between 24 and 48 hours after vaccine administration for adverse event monitoring.

TABLE 8

Time and Events Schedule: Treatment Period

| | Study Visit | | |
|---|---|---|---|
| Procedure | Pre-Pneumovax Visits | During Treatment Pneumovax Visit 1[a] | During Treatment Pneumovax Visit 2[b] |
| Pneumococcal Vaccine Informed Consent | X[c] | | |
| Pneumococcal Vaccine Blood Sample Collection | | X | X[d] |
| Immunization with Pneumococcal Vaccine | | X | |
| Adverse Event Monitoring | | X | |

[a]Pneumovax Visit 1may occur anytime after the subject has received at least 4 infusions of CTLA4Ig and has provided written informed consent. This visit should be scheduled to occur 7 ± 3 days prior to the subject's next regularly scheduled infusion. A regularly scheduled infusion for the main study will occur between Pneumovax Visit 1 and Visit 2.
[b]Pneumovax Visit 2 to occur on the day of the subject's subsequent regularly scheduled infusion; 28 days after the prior dose; 35 days after Pneumovax Visit 1.
[c]Informed consent for the pneumovax vaccine testing may be obtained at any time during the trial PRIOR to the collection of the first pneumococcal vaccine blood sample (for the purpose of obtaining CTLA4Ig trough levels and titers to the relevant pneumococcal serotypes).
[d]Blood sample to be collected immediately prior to the CTLA4Ig infusion.

Pharmacodynamic activity of CTLA4Ig will be derived from an assessment of CTLA4Ig's effect on the immune responses, as determined by measurement of antibody responses to 23-valent pneumococcal vaccines (Danish types: 2, 6B, 8, 9V, 14, 19F, and 23F). The primary analysis will be the percentage of subjects who demonstrate at least a two-fold increase in titer from pre-immunization. Confidence intervals will also be provided. All recorded adverse events will be listed and tabulated by the system organ class, preferred term and treatment. Summary statistics will be tabulated for anti-pneumococcal antibodies and the corresponding changes in antibody levels from baseline (pre-vaccination). Geometric means and coefficients of variations (%) will be reported for antibody concentrations. For each antibody, point estimates and 95% confidence intervals will be constructed for the geometric mean changes from pre-vaccination to post-vaccination antibody levels. These will be constructed from the results of repeated measures analyses of covariance on the natural logarithm of the antibody levels, with treatment group and study day as factors and the log of the baseline (pre-vaccination) antibody level as the covariate. For each antibody, point estimates and 95% confidence limits for the pre to post vaccination (post-pre) changes on the log scale will be exponentiated to obtain estimates for geometric means and ratios of geometric means on the original scale.

Pneumovax® 23 Vaccine will be obtained by study sites from Merck Laboratories. CTLA4Ig (Abatacept) will be obtained from Bristol Myers Squibb. The sub-set of subjects will receive 575 mcg/0.5 mL intramuscular or subcutaneous injection (in either the deltoid or lateral mid-thigh) of 23-valent pneumococcal vaccine according to Merck Laboratories package inserts. CTLA4Ig will be dosed as described above based on the subjects weight.

Example 3

The effect of CTLA4Ig (Abatacept, Bristol Myers Squibb) on the antibody response following immunization of RA subjects with the 23-valent pneumococcal vaccine, Pneumovax®, is currently being evaluated in a sub-study of an ongoing Phase III clinical trial, as described in Example 2. The objective of this uncontrolled sub-study is to provide preliminary data on the response to Pneumovax immunizations in CTLA4Ig-treated RA subjects (with an inadequate response to anti-TNF therapy and who are also on stable background DMARD therapy) who are receiving multiple doses of CTLA4Ig. For this sub-study, the relevant serotypes evaluated were Danish types 2, 6B, 8, 9V, 14, 19F, and 23F. As described in Example 2, subjects received their immunizations 7 days prior to their regularly scheduled CTLA4Ig infusion. Antibody titers were evaluated in all subjects prior to vaccine administration and again at ~35 days after vaccination. A response is considered positive when post-immunization antibody titers are ≧2-fold above baseline values.

Table 9 summarizes the demography of the 12 available subjects in the sub-study database, the co-administered DMARDs (including dose, route of administration, and frequency) at the time of immunizations, and the number of serotypes each patient responded to with post-immunization antibody titers that were ≧2-fold over baseline.

TABLE 9

Demography and Concomitant Medication(s) at the Time of Immunization

| Patient ID | Age (Yrs) | Concomitant Medications | Dose | Route and Frequency | No. of Serotypes Responded to With ≧ 2-Fold Increase Over Baseline |
|---|---|---|---|---|---|
| 1 | 67 | Methotrexate | 5-7.5 mg | PO: Weekly | 7/7 |
| 2 | 58 | Methotrexate | 15 mg | PO: Weekly | 2/7 |
| 3 | 57 | Methotrexate | 17.5 mg | SC: Weekly | 0/7 |
|   |    | Hydroxychloroquine | 400 mg | PO: QD |   |
| 4 | 50 | Methotrexate | 17.5 mg | PO: Weekly | 1/7 |
|   |    | Plaquenil | 400 mg | PO: QD |   |
| 5 | 53 | Methotrexate | 22.5 mg | PO: Weekly | 2/7 |
| 6 | 46 | Methotrexate | 25 mg | PO: Weekly | 5/7 |
| 7 | 53 | Leflunomide | 20 mg | PO: EOD | 3/7 |
| 8 | 29 | Methotrexate | 12.5-15 mg | PO: Weekly | 3/7 |
| 9 | 37 | Anakinra | 100 mg | SC: QD | 2/7 |
|   |    | Methotrexate | 15 mg | PO: Weekly |   |
| 10 | 79 | Methotrexate | 7.5 mg | PO: Weekly | 0/7 |
| 11 | 55 | Methotrexate | 5-7.5 mg | PO: Weekly | 7/7 |
| 12 | 49 | Methotrexate | 17.5 mg | PO: Weekly | 0/7 |

The patients were between 29 and 79 years old and all were receiving background MTX. Overall, the preliminary data from this small sub-study showed that 33% (4 of 12) of subjects responded to either none or only 1 of the 7 pneumococcal serotypes tested, 8 of 12 (67%) subjects responded to at least 2 serotypes, and 2 of 12 (17%) subjects responded to all 7 serotypes (Table 9). Response to the 23-valent pneumococcal vaccine was also not uniformly immunogenic in these patients. Evaluation of each individual serotype revealed that 58%, 33%, 50%, 25%, 41%, 16%, and 41% of subjects responded with ≧2-fold increase over baseline to serotype 2, 6B, 8, 9V, 14, 19F, and 23F, respectively, at ~1 month post-immunization.

Conclusions

In the 12 patients in this sub-study, 67% of patients mounted a response to at least two serotypes. to pneumococcal vaccine All patients analyzed were receiving concomitant MTX, the use of which has been linked with a decreased response among RA subjects who were being treated with concomitant MTX.

Example 4

The safety and efficacy of CTLA4Ig (Abatacept, Bristol Myers Squibb) has been demonstrated in RA patients with an inadequate response to anti-TNF therapy receiving background DMARDs. A study in healthy volunteers suggested that while CTLA4Ig may blunt immune responses to vaccination, the ability to mount a clinically relevant vaccination response is not impaired. This sub-study evaluated the immune response to influenza immunization in patients with active RA being treated with CTLA4Ig in the Abatacept Researched in RA patients with an Inadequate anti-TNF response to Validate Effectiveness (ARRIVE) trial.

ARRIVE was an international, 6-month, open-label Phase IIIb trial of patients with active RA and an inadequate response to ≧3 months of anti-TNF therapy. CTLA4Ig was administered by IV infusion at ~10 mg/kg on Days 1, 15 and 29, and every 4 weeks thereafter, ± background non-biologic DMARD. A sub-analysis was performed in 20 patients to evaluate the response to influenza vaccination in patients who had received CTLA4Ig for ≧3 months. Patients were immunized with the WHO trivalent influenza vaccine containing strains: H1N1; H3N2; and influenza B. Vaccination took place 7 days prior to a CTLA4Ig dose; serum was collected ~35 days later and antibody responses were assessed using a serum dilution assay format. A 4-fold increase in antibody titre relative to baseline was considered a positive response. Trough serum samples were collected prior to CTLA4Ig dosing on Day 7, and CTLA4Ig concentrations were measured using a validated ELISA method.

Seventy five percent of patients mounted a response to at least 1 influenza strain, half of all patients assessed (50%) mounted a response to 2 or more strains (Table). Five patients (25%) did not mount a response to any of the influenza strains. Eleven (55%), 10 (50%) and 7 (35%) patients mounted a response to the H1N1, H3N2 and Influenza B strains, respectively. CTLA4Ig serum concentrations did not appear to be linked to the ability to mount a response to influenza vaccination.

Table 10 describes the number and percentage of patients that responded to 0, at least 1, at least 2 or all 3 of the influenza strains utilized in the immunization.

TABLE 10

|  | Number of influenza strains responded to | | | |
|---|---|---|---|---|
|  | 0 | ≧1 | ≧2 | 3 |
| Patients, n (%) | 5 (25%) | 15 (75%) | 10 (50%) | 3 (15%) |

Conclusion

Seventy five percent of CTLA4Ig-treated RA patients responded to at least one strain, demonstrating that CTLA4Ig does not abrogate the ability of RA patients to mount an immune response to influenza immunization.

What is claimed is:

1. A method of vaccinating a subject being treated with soluble CTLA4 molecule comprising administering a vaccine 14±3 days prior to the administration of the soluble CTLA4 molecule dose, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356 or L104EA29YIg as shown in FIG. 8 beginning with methionine at position +1 or with alanine at position −1 and ending with lysine at position +357 or glycine at position +356.

2. The method according to claim 1 wherein the soluble CTLA4 molecule is administered in an amount between about 0.1 and about 20.0 mg/kg weight of the subject.

3. A method of vaccinating a subject being treated with soluble CTLA4 molecule comprising administering a vaccine 14±3 days after the administration of the soluble CTLA4 molecule dose, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356 or L104EA29YIg as shown in FIG. 8 beginning with methionine at position +1 or with alanine at position −1 and ending with lysine at position +357 or glycine at position +356.

4. The method according to claim 3 wherein the soluble CTLA4 molecule is administered in an amount between about 0.1 and about 20.0 mg/kg weight of the subject.

5. A method of vaccinating a subject being treated with soluble CTLA4 molecule comprising administering a vaccine 7±3 days prior to the administration of the soluble CTLA4 molecule dose, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356 or L104EA29YIg as shown in FIG. 8 beginning with methionine at position +1 or with alanine at position −1 and ending with lysine at position +357 or glycine at position +356.

6. The method according to claim 5 wherein the soluble CTLA4 molecule is administered in an amount between about 0.1 and about 20.0 mg/kg weight of the subject.

7. A method of vaccinating a subject being treated with soluble CTLA4 molecule comprising administering a vaccine at least 4 days prior to the administration of the soluble CTLA4 molecule dose, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356 or L104EA29YIg as shown in FIG. 8 beginning with methionine at position +1 or with alanine at position −1 and ending with lysine at position +357 or glycine at position +356.

8. The method according to claim 7 wherein the soluble CTLA4 molecule is administered in an amount between about 0.1 and about 20.0 mg/kg weight of the subject.

9. A method of vaccinating a subject being treated with soluble CTLA4 molecule comprising administering a vaccine at a low point of the effective serum trough concentration of the soluble CTLA4 molecule, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356 or L104EA29YIg as shown in FIG. 8 beginning with methionine at position +1 or with alanine at position −1 and ending with lysine at position +357 or glycine at position +356.

10. The method according to claim 9 wherein the effective trough serum concentration of the soluble CTLA4 molecules is between about 0.2 μg/mL and about 70 μg/mL.

11. A method of vaccinating a subject being treated with soluble CTLA4 molecule comprising administering a vaccine 7±3 days prior to the administration of the soluble CTLA4 molecule dose, wherein the vaccine is selected from the group consisting of influenza vaccine, pneumococcal vaccine and tetanus toxoid vaccine, wherein the soluble CTLA4 molecule is CTLA4Ig as shown in FIG. 6 beginning with methionine at position +1 or with alanine at position −1 and ending with lysine at position +357 or glycine at position +356, and wherein the CTLA4Ig dose is 500 mg for a subject weighing less than 60 kg, 750 mg for a subject weighting between 60 -100 kg and 1000mg for a subject weighing more than 100 kg.

12. A method of vaccinating a subject being treated with soluble CTLA4 molecule comprising administering a vaccine 7±3 days prior to the administration of the soluble CTLA4 molecule dose, wherein the vaccine is selected from the group consisting of influenza vaccine, pneumococcal vaccine and tetanus toxoid vaccine, wherein the soluble CTLA4 molecule is L104EA29YIg as shown in FIG. 8 beginning with methionine at position +1 or with alanine at position −1 and ending with lysine at position +357 or glycine at position +356, and wherein the L104EA29YIg dose is 5 mg/kg weight of the subject.

\* \* \* \* \*

UNITED STATES PATENT AND TRADEMARK OFFICE
CERTIFICATE OF CORRECTION

PATENT NO. : 7,528,111 B2  
APPLICATION NO. : 11/800860  
DATED : May 5, 2009  
INVENTOR(S) : George Vratsanos et al.

Page 1 of 1

It is certified that error appears in the above-identified patent and that said Letters Patent is hereby corrected as shown below:

Column 3 Line 14  
moleucle should read "molecule"

Column 16 Table 4  
under "Treatment D"  
    N-20  
     36  
     13  
    20-55     should read "20-56"

Column 22 Line 50  
respondres should read "responders"

Signed and Sealed this

Eighteenth Day of August, 2009

David J. Kappos  
*Director of the United States Patent and Trademark Office*

UNITED STATES PATENT AND TRADEMARK OFFICE
CERTIFICATE OF CORRECTION

PATENT NO. : 7,528,111 B2
APPLICATION NO. : 11/800860
DATED : May 5, 2009
INVENTOR(S) : George Vratsanos et al.

It is certified that error appears in the above-identified patent and that said Letters Patent is hereby corrected as shown below:

On the Title page, item [56]:
Column 2 (Other Publications)
Line 1
    Delete "Arthtritis" and insert -- Arthritis --
Line 2
    Delete "LInsley" and insert -- Linsley, --

Column 3
Line 14
    moleucle should read "molecule"

Column 16
Table 4
    under "Treatment D"
        N-20
         36
         13
        20-55      should read "20-56"

Column 22
Line 50
    respondres should read "responders"

Column 35
Line 42
    In Claim 1, delete "CTLA4lg" and insert -- CLTA4Ig --
Line 45
    In Claim 1, delete "L104EA29Ylg" and insert -- L104EA29YIg --
Line 59
    In Claim 3, delete "CTLA4lg" and insert -- CTLA4Ig --
Line 62
    In Claim 3, delete "L104EA29Ylg" and insert -- L104EA29YIg --

UNITED STATES PATENT AND TRADEMARK OFFICE
CERTIFICATE OF CORRECTION

PATENT NO. : 7,528,111 B2
APPLICATION NO. : 11/800860
DATED : May 5, 2009
INVENTOR(S) : George Vratsanos et al.

It is certified that error appears in the above-identified patent and that said Letters Patent is hereby corrected as shown below:

Column 36
Line 41
    In Claim 5, delete "CTLA4lg" and insert -- CTLA4Ig --
Line 44
    In Claim 5, delete "L104EA29Ylg" and insert -- L104EA29YIg --
Line 61
    In Claim 7, delete "L104EA29Ylg" and insert -- L104EA29YIg --

Column 37
Line 10
    In Claim 9, delete "L104EA28Ylg" and insert -- L104EA29YIg --

Column 38
Line 15
    In Claim 12, delete "L104EA28Ylg" and insert -- L104EA29YIg --
Line 18
    In Claim 12, delete "L104EA28Ylg" and insert -- L104EA29YIg --

Signed and Sealed this

First Day of September, 2009

David J. Kappos
*Director of the United States Patent and Trademark Office*

SEQUENCE LISTING

<160> NUMBER OF SEQ ID NOS: 6

<210> SEQ ID NO 1
<211> LENGTH: 1152
<212> TYPE: DNA
<213> ORGANISM: Artificial Sequence
<220> FEATURE:
<223> OTHER INFORMATION: CTLA4Ig

<400> SEQUENCE: 1

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca agccactga ggtccgggtg      180 acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg actctacat ctgcaaggtg      360 gagctcatgt accaccgcc atactacctg gcataggca acggaaccca gatttatgta       420
attgatccag aaccgtgccc agattctgat caggagccca atcttctga caaaactcac      480 acatccccac cgtccccagc acctgaactc ctggtggat cgtcagtctt cctcttcccc      540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg ggtggtcagc     720
gtcctcaccg tcctgcacca ggactggctg aatggcaagg agtacaagtg caaggtctcc     780
aacaaagccc tcccagcccc catcgagaaa accatctcca agccaaagg gcagccccga      840 gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

<210> SEQ ID NO 2
<211> LENGTH: 383
<212> TYPE: PRT
<213> ORGANISM: Artificial Sequence
<220> FEATURE:
<223> OTHER INFORMATION: CTLA4Ig

<400> SEQUENCE: 2

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80
```

-continued

| | | | | | | | | | | | |
|---|---|---|---|---|---|---|---|---|---|---|---|
|Gly|Asn|Glu|Leu|Thr|Phe|Leu|Asp|Asp|Ser|Ile|Cys|Thr|Gly|Thr|Ser|
| | | | |85| | | |90| | | |95| | | |

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 3
<211> LENGTH: 636
<212> TYPE: DNA
<213> ORGANISM: Artificial Sequence
<220> FEATURE:
<223> OTHER INFORMATION: CTLA4 RECEPTOR

<400> SEQUENCE: 3
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcca gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360

```
gagctcatgt acccaccgcc atactacctg ggcataggca acggaaccca gatttatgta    420
attgatccag aaccgtgccc agattctgac ttcctcctct ggatccttgc agcagttagt    480
tcggggttgt ttttttatag ctttctcctc acagctgttt ctttgagcaa aatgctaaag    540
aaaagaagcc ctcttacaac aggggtctat gtgaaaatgc ccccaacaga gccagaatgt    600
gaaaagcaat ttcagcctta ttttattccc atcaat                              636
```

<210> SEQ ID NO 4
<211> LENGTH: 212
<212> TYPE: PRT
<213> ORGANISM: Artificial Sequence
<220> FEATURE:
<223> OTHER INFORMATION: CTLA4 RECEPTOR

<400> SEQUENCE: 4

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
                20                  25                  30

Ala Val Val Leu Ala Ser Ser Arg Gly Ile Ala Ser Phe Val Cys Glu
            35                  40                  45

Tyr Ala Ser Pro Gly Lys Ala Thr Glu Val Arg Val Thr Val Leu Arg
        50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Phe Leu Leu Trp Ile Leu Ala Ala Val Ser
145                 150                 155                 160

Ser Gly Leu Phe Phe Tyr Ser Phe Leu Leu Thr Ala Val Ser Leu Ser
                165                 170                 175

Lys Met Leu Lys Lys Arg Ser Pro Leu Thr Thr Gly Val Tyr Val Lys
            180                 185                 190

Met Pro Pro Thr Glu Pro Glu Cys Glu Lys Gln Phe Gln Pro Tyr Phe
        195                 200                 205

Ile Pro Ile Asn
    210
```

<210> SEQ ID NO 5
<211> LENGTH: 1152
<212> TYPE: DNA
<213> ORGANISM: Artificial Sequence
<220> FEATURE:
<223> OTHER INFORMATION: L104EA29YIg

<400> SEQUENCE: 5

```
atgggtgtac tgctcacaca gaggacgctg ctcagtctgg tccttgcact cctgtttcca    60
agcatggcga gcatggcaat gcacgtggcc cagcctgctg tggtactggc cagcagccga    120
ggcatcgcta gctttgtgtg tgagtatgca tctccaggca aatatactga ggtccgggtg    180
acagtgcttc ggcaggctga cagccaggtg actgaagtct gtgcggcaac ctacatgatg    240
```

```
gggaatgagt tgaccttcct agatgattcc atctgcacgg gcacctccag tggaaatcaa    300
gtgaacctca ctatccaagg actgagggcc atggacacgg actctacat ctgcaaggtg     360 gagctcatgt acccaccgcc atactacgag ggcataggca acggaaccca gatttatgta    420
attgatccag aaccgtgccc agattctgat caggagccca atcttctga caaaactcac     480 acatccccac cgtccccagc acctgaactc ctggggggat cgtcagtctt cctcttcccc    540
ccaaaaccca aggacaccct catgatctcc cggacccctg aggtcacatg cgtggtggtg    600
gacgtgagcc acgaagaccc tgaggtcaag ttcaactggt acgtggacgg cgtggaggtg    660
cataatgcca agacaaagcc gcgggaggag cagtacaaca gcacgtaccg tgtggtcagc    720
gtcctcaccg tcctgcacca ggactggctg aatggcaagg agtacaagtg caaggtctcc    780
aacaaagccc tcccagcccc catcgagaaa accatctcca aagccaaagg cagccccga    840 gaaccacagg tgtacaccct gcccccatcc cgggatgagc tgaccaagaa ccaggtcagc    900
ctgacctgcc tggtcaaagg cttctatccc agcgacatcg ccgtggagtg ggagagcaat    960
gggcagccgg agaacaacta caagaccacg cctcccgtgc tggactccga cggctccttc   1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct   1140
ccgggtaaat ga                                                        1152
```

<210> SEQ ID NO 6
<211> LENGTH: 383
<212> TYPE: PRT
<213> ORGANISM: Artificial Sequence
<220> FEATURE:
<223> OTHER INFORMATION: L104EA29YIg

<400> SEQUENCE: 6

```
Met Gly Val Leu Leu Thr Gln Arg Thr Leu Leu Ser Leu Val Leu Ala
1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Tyr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190
```

-continued

```
Pro Glu Val Thr Cys Val Val Asp Val Ser His Glu Asp Pro Glu
        195             200             205
Val Lys Phe Asn Trp Tyr Val Asp Gly Val Glu Val His Asn Ala Lys
    210             215             220
Thr Lys Pro Arg Glu Glu Gln Tyr Asn Ser Thr Tyr Arg Val Val Ser
225             230             235             240
Val Leu Thr Val Leu His Gln Asp Trp Leu Asn Gly Lys Glu Tyr Lys
            245             250             255
Cys Lys Val Ser Asn Lys Ala Leu Pro Ala Pro Ile Glu Lys Thr Ile
            260             265             270
Ser Lys Ala Lys Gly Gln Pro Arg Glu Pro Gln Val Tyr Thr Leu Pro
        275             280             285
Pro Ser Arg Asp Glu Leu Thr Lys Asn Gln Val Ser Leu Thr Cys Leu
    290             295             300
Val Lys Gly Phe Tyr Pro Ser Asp Ile Ala Val Glu Trp Glu Ser Asn
305             310             315             320
Gly Gln Pro Glu Asn Asn Tyr Lys Thr Thr Pro Pro Val Leu Asp Ser
            325             330             335
Asp Gly Ser Phe Phe Leu Tyr Ser Lys Leu Thr Val Asp Lys Ser Arg
            340             345             350
Trp Gln Gln Gly Asn Val Phe Ser Cys Ser Val Met His Glu Ala Leu
        355             360             365
His Asn His Tyr Thr Gln Lys Ser Leu Ser Leu Ser Pro Gly Lys
    370             375             380
```